US011324385B2

(12) United States Patent
Oka

(10) Patent No.: US 11,324,385 B2
(45) Date of Patent: May 10, 2022

(54) ENDOSCOPE SYSTEM FOR PROCESSING SECOND ILLUMINATION IMAGE USING IMAGE INFORMATION OTHER THAN IMAGE INFORMATION ABOUT OUTERMOST SURFACE SIDE OF SUBJECT AMONG THREE IMAGE INFORMATION FROM AT LEAST FOUR IMAGES OF FIRST ILLUMINATION IMAGES

(71) Applicant: OLYMPUS CORPORATION, Tokyo (JP)

(72) Inventor: Tetsuhiro Oka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 242 days.

(21) Appl. No.: 16/702,839

(22) Filed: Dec. 4, 2019

(65) Prior Publication Data

US 2020/0100650 A1 Apr. 2, 2020

Related U.S. Application Data

(63) Continuation of application No. PCT/JP2017/021665, filed on Jun. 12, 2017.

(51) Int. Cl.
*A61B 1/00* (2006.01)
*A61B 1/05* (2006.01)
(Continued)

(52) U.S. Cl.
CPC ............ *A61B 1/00009* (2013.01); *A61B 1/05* (2013.01); *A61B 1/063* (2013.01); *A61B 1/00045* (2013.01); *A61B 1/0676* (2013.01); *A61B 1/07* (2013.01)

(58) Field of Classification Search
CPC ....... A61B 1/00009; A61B 1/05; A61B 1/063; A61B 1/00045; A61B 1/0676; A61B 1/07; G02B 23/2461; G02B 23/2484
See application file for complete search history.

(56) References Cited

U.S. PATENT DOCUMENTS 6,464,633 B1 * 10/2002 Hosoda ................ A61B 1/0638
348/68
7,519,096 B2 4/2009 Bouma et al.
(Continued)

FOREIGN PATENT DOCUMENTS

EP 2229870 A1 9/2010
EP 2520214 A1 11/2012
(Continued)

OTHER PUBLICATIONS

International Search Report dated Jul. 24, 2018 issued in International Application No. PCT/JP2018/021590, with partial English translation.
(Continued)

*Primary Examiner* — Aaron B Fairchild
*Assistant Examiner* — Shankar Raj Ghimire
(74) *Attorney, Agent, or Firm* — Scully, Scott, Murphy & Presser, P.C.

(57) ABSTRACT

An endoscope system according to the present invention includes: a first illuminating portion that emits first illumination lights having low-spatial-frequency and high-spatial-frequency and changes the intensity distribution of the first illumination lights over time; a second illuminating portion that emits a second illumination light; an imaging unit that images first and second illumination images of an subject respectively illuminated by the first and second illumination lights; and an image-processing portion that processes the first and second illumination images. The imaging unit images four images including images that correspond to the
(Continued)

first illumination lights having low-spatial-frequency and high-spatial-frequency and images in which light and dark portions of the first illumination lights are exchanged with each other. The image-processing portion separates three image information for different depths, and processes the second illumination image by the image information other than the image information about the outermost surface side.

10 Claims, 19 Drawing Sheets

(51) Int. Cl.
  *A61B 1/06* (2006.01)
  *A61B 1/07* (2006.01)

(56) References Cited

U.S. PATENT DOCUMENTS

| | | | | |
|---|---|---|---|---|
| 8,570,625 | B2* | 10/2013 | Kempe | G02B 21/0032 |
| | | | | 358/509 |
| 10,251,530 | B2* | 4/2019 | Henley | A61B 1/00006 |
| 10,342,459 | B2* | 7/2019 | Yokota | A61B 1/00009 |
| 10,972,675 | B2* | 4/2021 | Shinji | H04N 5/2354 |
| 11,045,081 | B2* | 6/2021 | Matsumoto | A61B 1/0669 |
| 11,070,739 | B2* | 7/2021 | Matsumoto | A61B 1/00096 |
| 2002/0165456 | A1 | 11/2002 | Canpolat et al. | |
| 2009/0058999 | A1* | 3/2009 | Gono | G01J 3/50 |
| | | | | 348/71 |
| 2010/0048995 | A1 | 2/2010 | Suijver et al. | |
| 2010/0195078 | A1 | 8/2010 | Horiuchi et al. | |
| 2010/0224796 | A1* | 9/2010 | Mertz | G02B 21/0076 |
| | | | | 250/459.1 |
| 2010/0240953 | A1 | 9/2010 | Murakami | |
| 2010/0245551 | A1 | 9/2010 | Morita | |
| 2011/0263955 | A1 | 10/2011 | Narita et al. | |
| 2012/0123205 | A1 | 5/2012 | Nie et al. | |
| 2012/0302847 | A1 | 11/2012 | Ozawa et al. | |
| 2012/0327205 | A1 | 12/2012 | Takahashi | |
| 2013/0270421 | A1 | 10/2013 | Kanamori et al. | |
| 2014/0052005 | A1 | 2/2014 | Yokota | |
| 2014/0092227 | A1 | 4/2014 | Kanamori et al. | |
| 2014/0267657 | A1 | 9/2014 | Takei et al. | |
| 2014/0316283 | A1* | 10/2014 | Kaku | A61B 1/0638 |
| | | | | 600/479 |
| 2015/0022647 | A1 | 1/2015 | Takei et al. | |
| 2015/0238089 | A1 | 8/2015 | Fujinuma et al. | |
| 2015/0320296 | A1 | 11/2015 | Morita | |
| 2016/0041334 | A1 | 2/2016 | Suijver et al. | |
| 2016/0278678 | A1 | 9/2016 | Valdes et al. | |
| 2016/0334340 | A1 | 11/2016 | Ollivier et al. | |
| 2017/0006202 | A1 | 1/2017 | Otani et al. | |
| 2017/0098301 | A1 | 4/2017 | Ikemoto et al. | |
| 2017/0231480 | A1 | 8/2017 | Yamazaki | |
| 2018/0164221 | A1 | 6/2018 | Singh et al. | |
| 2020/0099844 | A1 | 3/2020 | Shinji et al. | |
| 2020/0099845 | A1 | 3/2020 | Matsumoto et al. | |
| 2020/0100650 | A1* | 4/2020 | Oka | A61B 1/063 |
| 2020/0100660 | A1 | 4/2020 | Matsumoto et al. | |

FOREIGN PATENT DOCUMENTS

| | | |
|---|---|---|
| EP | 2526854 A1 | 11/2012 |
| EP | 2979607 A1 | 2/2016 |
| EP | 3075301 A1 | 10/2016 |
| EP | 3202306 A1 | 8/2017 |
| JP | 2009-536066 A | 10/2009 |
| JP | 2010-213992 A | 9/2010 |
| JP | 2010-227256 A | 10/2010 |
| JP | 2012-239816 A | 12/2012 |
| JP | 2014-18439 A | 2/2014 |
| JP | 2014-188222 A | 10/2014 |
| JP | 2015-077415 A | 4/2015 |
| JP | 2015-231498 A | 12/2015 |
| JP | 2016-49370 A | 4/2016 |
| JP | 2016-174836 A | 10/2016 |
| JP | 2016-198304 A | 12/2016 |
| JP | 2016-200418 A | 12/2016 |
| JP | 2016-209466 A | 12/2016 |
| JP | 2017-042629 A | 3/2017 |
| WO | WO 2007/132378 A2 | 11/2007 |
| WO | WO 2011/080996 A1 | 7/2011 |
| WO | WO 2011/081141 A1 | 7/2011 |
| WO | WO 2015/016013 A1 | 2/2015 |
| WO | WO 2016/151903 A1 | 9/2016 |
| WO | WO 2016/181720 A1 | 11/2016 |
| WO | WO 2018/229831 A1 | 12/2018 |
| WO | WO 2018/229832 A1 | 12/2018 |
| WO | WO 2018/229834 A1 | 12/2018 |

OTHER PUBLICATIONS

International Search Report dated Jul. 24, 2018 issued in International Application No. PCT/JP2018/021597, with partial English translation.
Office Action dated Dec. 11, 2020 received in U.S. Appl. No. 16/691,961.
Office Action dated Dec. 3, 2020 received in U.S. Appl. No. 16/702,964.
International Search Report dated Aug. 22, 2017 issued in PCT/JP2017/021661.
International Search Report dated Aug. 15, 2017 issued in PCT/JP2017/021664.
International Search Report dated Aug. 22, 2017 issued in PCT/JP2017/021665.
International Search Report dated Aug. 22, 2017 issued in PCT/JP2017/021667.
Shree K. Nayar et al., "Fast separation of direct and global components of a scene using high frequency Illumination", ACM Transactions on Graphics (Jul. 3, 2006), vol. 25, Issue 3, pp. 935-944, cited in ISR.
T. Takatani et al., "Decomposition of Reflected and Scattered Lights by Multiple Weighted Measurements", 14th Symposium on Image Recognition and Understanding (MIRU2011) (Jul. 2011).
K. Tanaka et al., "Adaptive Frequency Selection under Parallel High-frequency Illumination", 16th Symposium on Image Recognition and Understanding (MIRU2013), Collection of Extended Abstract, Information Processing Society of Japan, Yoshiki Shimotsuma, SS2-33, cited in ISR.
T. Takatani et al.,"Decomposition of Reflected and Scattered Lights by Multiple Weighted Measurements", IPSJ SIG Technical Report (CD-ROM), vol. 2011, No. 1, ROMBUNNO.CVIM-177, No. 12, ISSN 2186-2583, cited in ISR.
Office Action dated Jun. 19, 2020 received in U.S. Appl. No. 16/691,865.

* cited by examiner

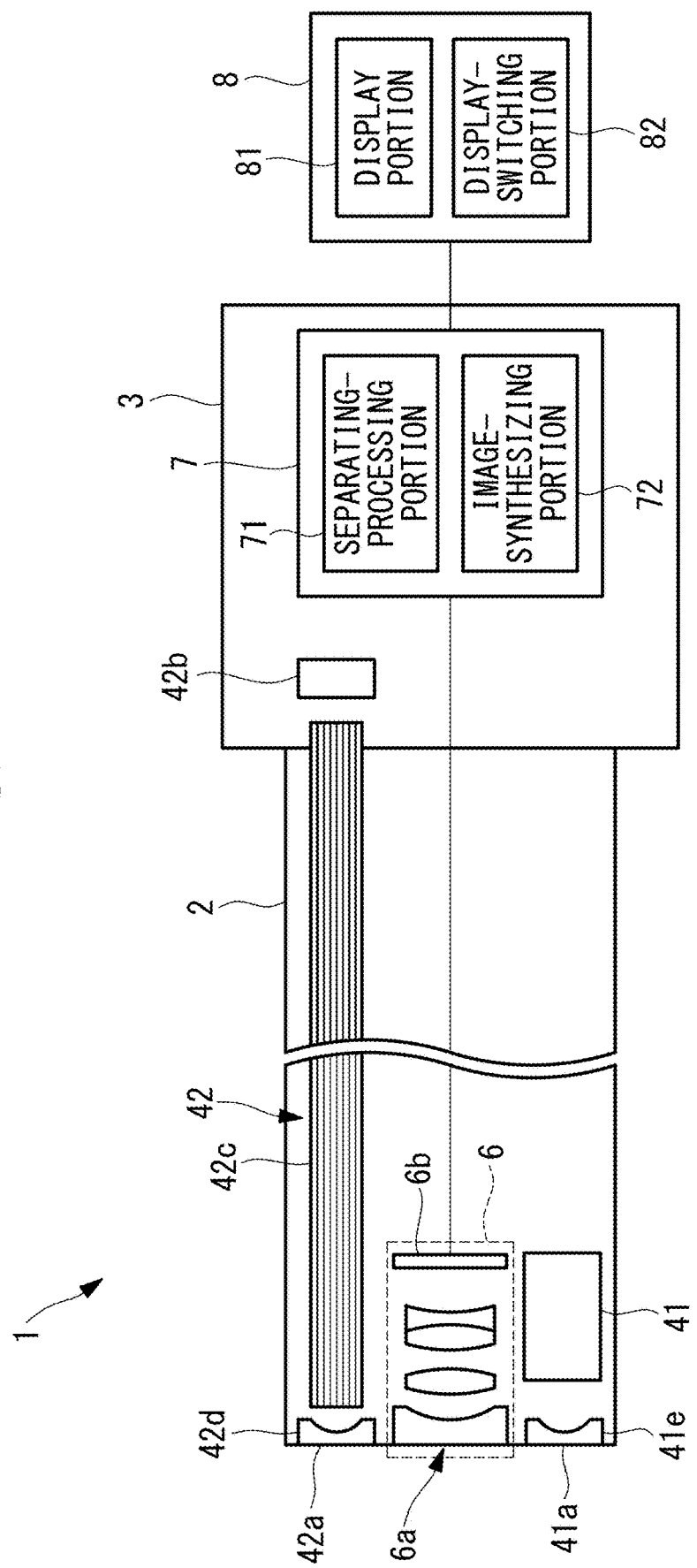

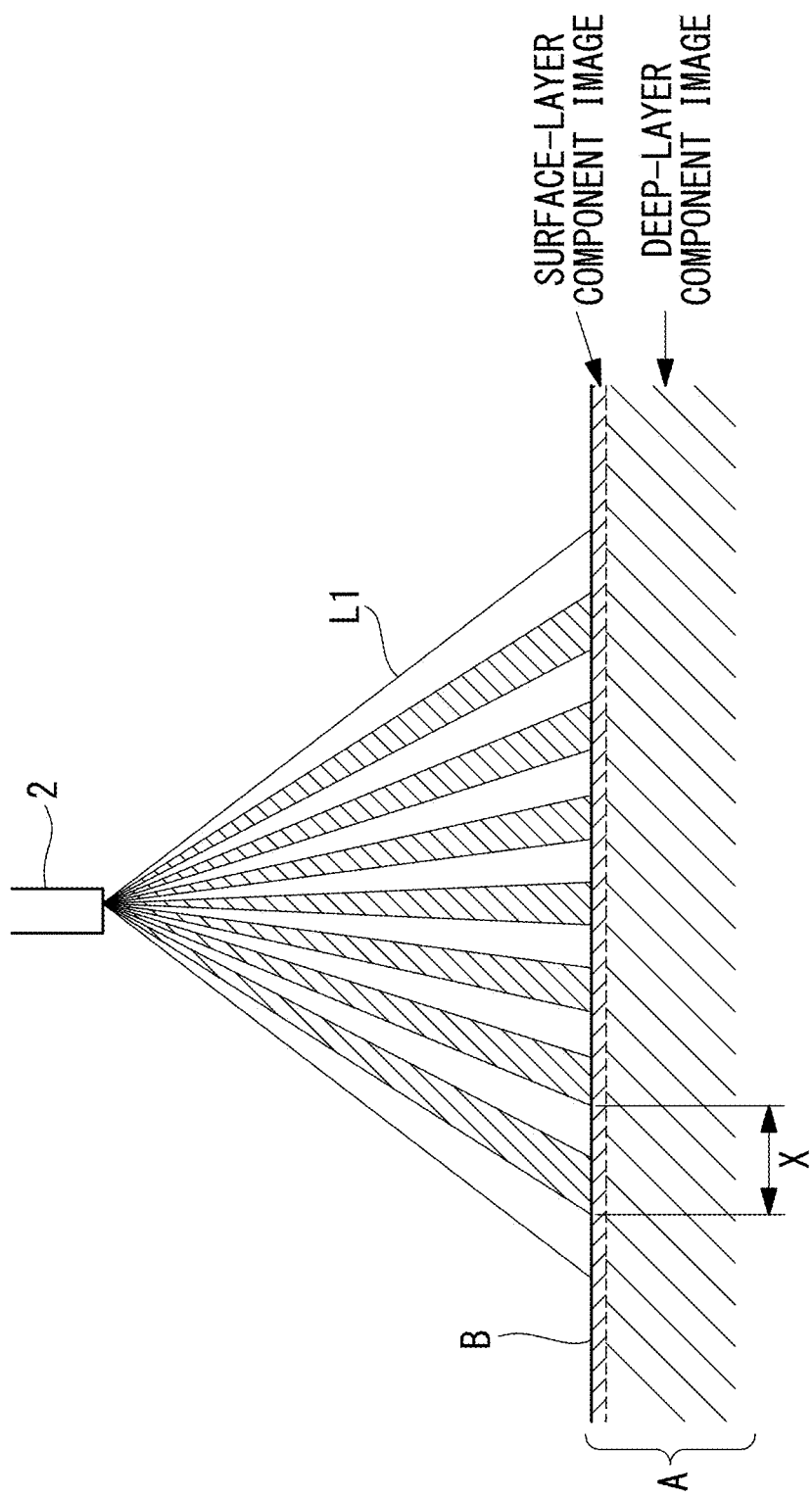

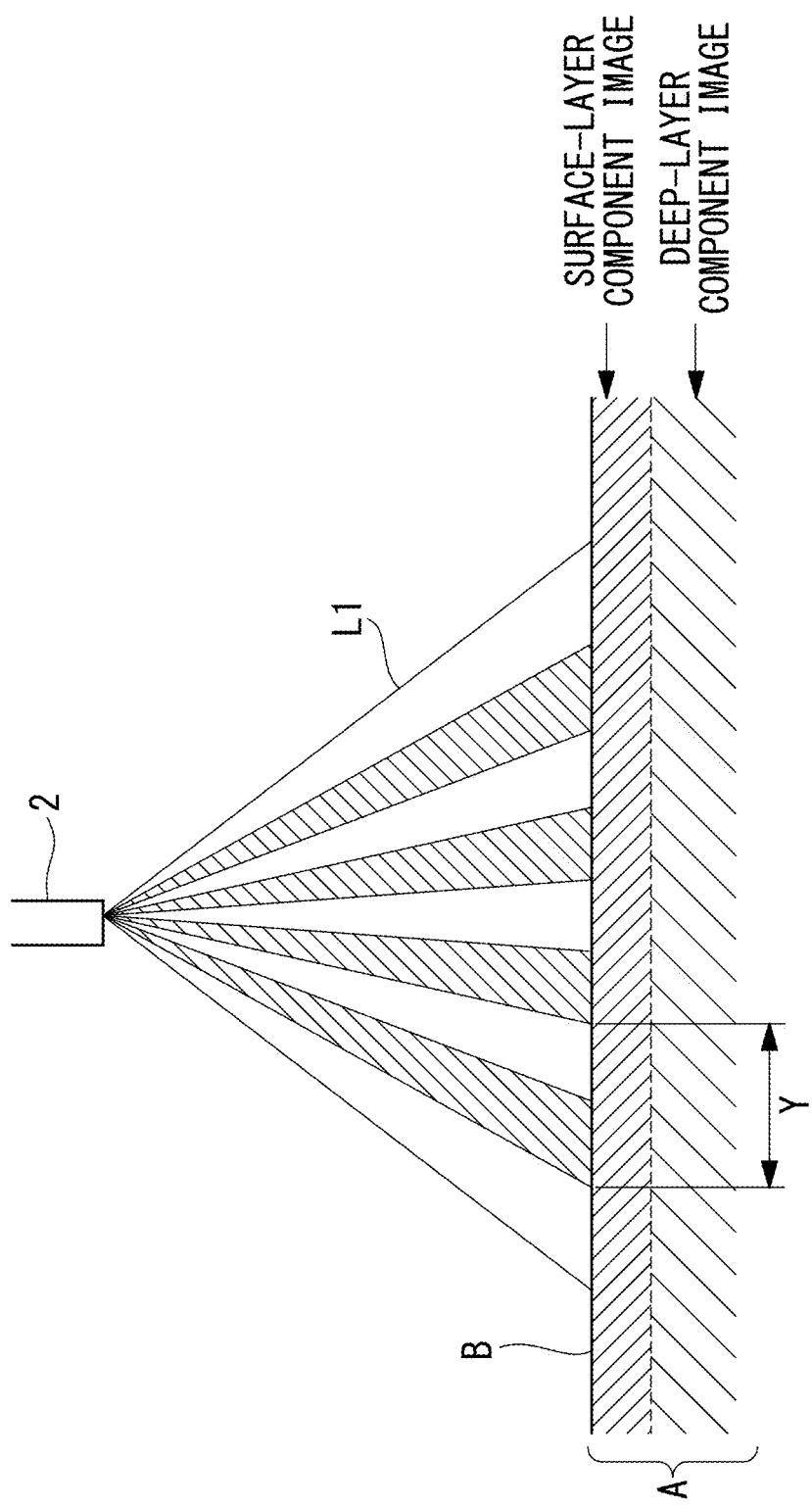

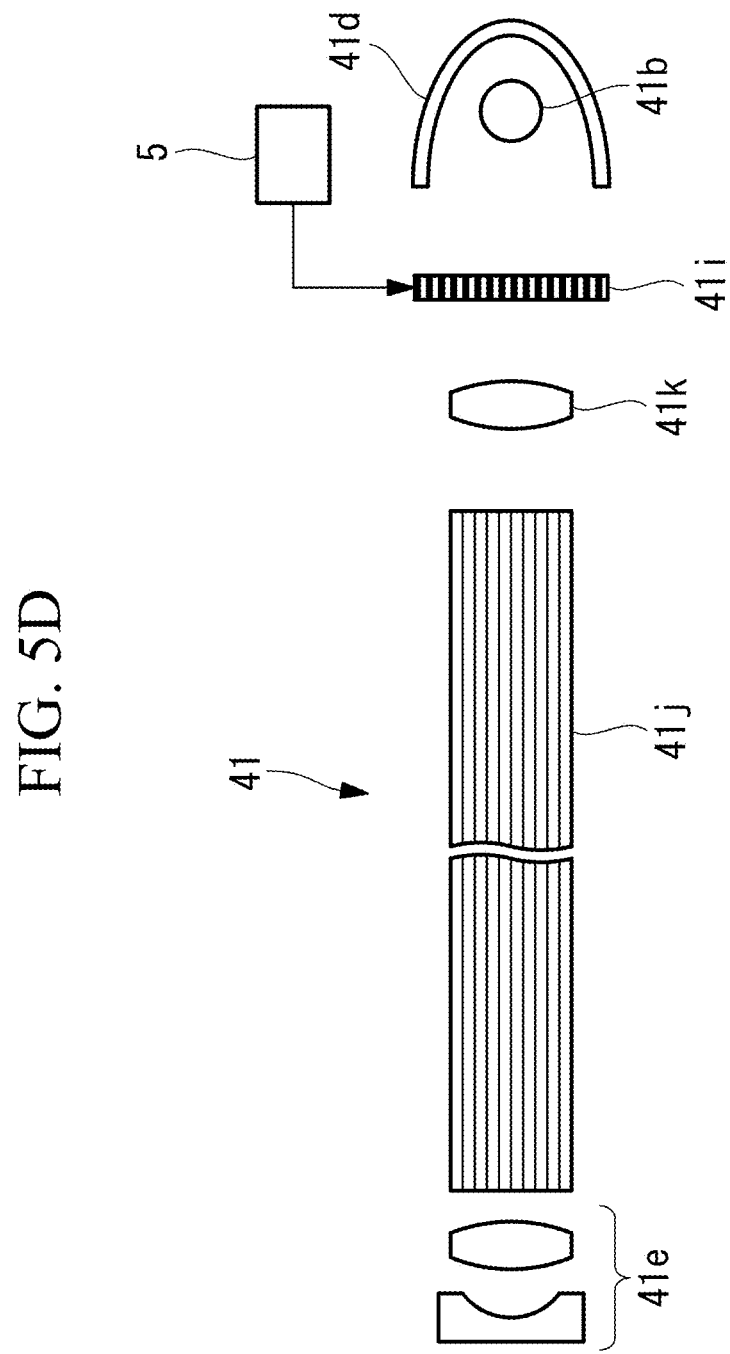

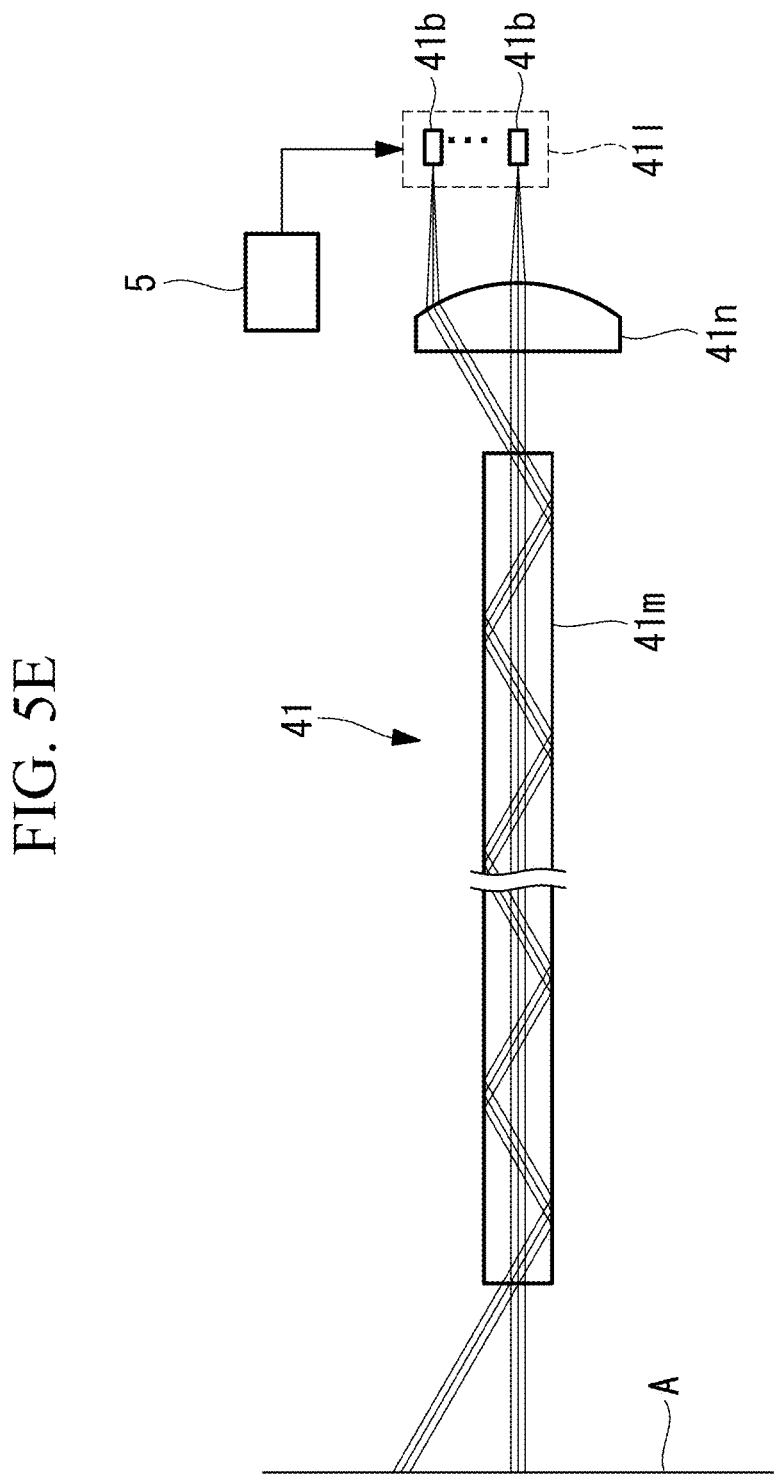

ENDOSCOPE SYSTEM FOR PROCESSING SECOND ILLUMINATION IMAGE USING IMAGE INFORMATION OTHER THAN IMAGE INFORMATION ABOUT OUTERMOST SURFACE SIDE OF SUBJECT AMONG THREE IMAGE INFORMATION FROM AT LEAST FOUR IMAGES OF FIRST ILLUMINATION IMAGES

CROSS-REFERENCE TO RELATED APPLICATIONS

This is a continuation of International Application PCT/JP2017/021665, with an international filing date of Jun. 12, 2017, which is hereby incorporated by reference herein in its entirety.

TECHNICAL FIELD

The present invention relates to an endoscope system.

BACKGROUND ART

Light generated in an illuminated object contains multiple types of components such as specular reflected (specular) light, diffuse reflected light, and scattered light. There is a proposed technology that separates information about a surface of the object and information about the interior of the object by separating such components contained in an image of the object by means of a high-frequency pattern projection method employing high-spatial-frequency structured illumination light (for example, see Non Patent Literature 1).

CITATION LIST

Non Patent Literature

{NPL 1} TAKATANI, Tsuyoshi, et al. "Decomposition of reflection and scattering by multi-weighted measurements", The 14th Meeting on Image Recognition and Understanding (MIRU2011) July 2011

SUMMARY OF INVENTION

A first aspect of is an endoscope system including: a first illuminating portion that radiates first illumination lights, which have a spatial intensity distribution in which light portions and dark portions are periodically repeated in a beam cross-section that is orthogonal to an optical axis, onto an subject from a first emitting surface; a second illuminating portion that radiates a second illumination light onto the subject from a second emitting surface that is different from the first emitting surface; an imaging unit that images first illumination images, which are images of the subject irradiated with the first illumination light, and a second illumination image, which is an image of the subject irradiated with the second illumination light; and an image-processing portion that processes the first illumination images and the second illumination image imaged by the imaging unit, wherein the first illuminating portion has an intensity-distribution changing portion that changes the intensity distribution over time so that positions of the light portions and the dark portions on a surface of the subject are exchanged with each other, and sequentially radiates a first illumination light having low-spatial-frequency, in which the spatial frequency of the intensity distribution is relatively low, and a first illumination light having high-spatial-frequency, in which the spatial frequency of the intensity distribution is relatively high, wherein the imaging unit images at least four images that serves as the first illumination images, wherein the at least four images include images that correspond to the first illumination light having low-spatial-frequency and the first illumination light having high-spatial-frequency, and two images in which the positions of the light portions and the dark portions are exchanged with each other by the intensity-distribution changing portion, and wherein the image-processing portion has a separating-processing portion that separates three of image information for different depths of the subject from the at least four images, and an image-synthesizing portion that processes the second illumination image by using image information other than the image information about the outermost surface side of the subject among the three of image information separated by the separating-processing portion.

A second aspect of the present invention is an endoscope system including: a first illuminating portion that sequentially radiates an illumination light, which includes linearly polarized light and has a spatial intensity distribution in which light portions and dark portions are periodically repeated in a beam cross-section that is orthogonal to an optical axis, and a spatially uniform illumination light onto an subject from a first emitting surface as a first illumination light; a second illuminating portion that radiates a second illumination light onto the subject from a second emitting surface that is different from the first emitting surface; an imaging unit that images first illumination images, which are images of the subject irradiated with the first illumination light, and a second illumination image, which is an image of the subject irradiated with the second illumination light; and an image-processing portion that processes the first illumination images and the second illumination image imaged by the imaging unit, wherein the first illuminating portion has an intensity-distribution changing portion that changes the intensity distribution over time so that positions of the light portions and the dark portions on a surface of the subject are exchanged with each other, wherein the imaging unit has a polarizing plate that has substantially the same polarizing direction as the polarizing direction of the first illumination light and that can be inserted into/retracted from an optical path, wherein the first illumination images include at least two images that are imaged when the polarizing plate is retracted from the optical path and in which the first illumination light that has the intensity distribution and in which the positions of the light portions and the dark portions are exchanged with each other by the intensity-distribution changing portion is radiated, and an image that is imaged when the polarizing plate is disposed on the optical path and in which the spatially uniform first illumination light is radiated, and wherein the image-processing portion has a separating-processing portion that separates three of image information for different depths of the subject from the at least four images, and an image-synthesizing portion that processes the second illumination image by using image information other than the image information about the outermost surface side of the subject among the three of image information separated by the separating-processing portion.

BRIEF DESCRIPTION OF DRAWINGS

FIG. 1 is an overall configuration diagram of an endoscope system according to an embodiment of the present invention.

FIG. 2A is a diagram showing the relationship between a first illumination light having high-spatial-frequency that is emitted from a first illuminating portion in FIG. 1 and depths that are included in information of a surface-layer component image and a deep-layer component image.

FIG. 2B is a diagram for explaining the relationship between a first illumination light having low-spatial-frequency that is emitted from the first illuminating portion in FIG. 1 and depths that are included in information of a surface-layer component image and a deep-layer component image.

FIG. 5D is a diagram showing another configuration example of a first illuminating unit and an intensity-distribution changing unit.

FIG. 5E is a diagram showing another configuration example of a first illuminating unit and an intensity-distribution changing unit.

DESCRIPTION OF EMBODIMENT

Figure 3A:
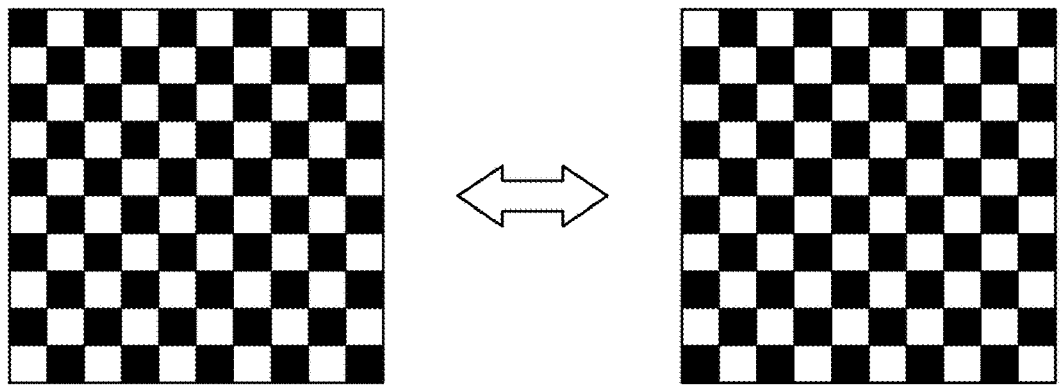
FIG. 3A is a diagram showing an example of the intensity distribution of the first illumination light and changes in the intensity pattern over time.

An endoscope system 1 according to an embodiment of the present invention will be described below with reference to the drawings.

As shown in FIG. 1, the endoscope system 1 according to this embodiment includes: an endoscope 2 for observing the body interior; and a main body 3 connected to a base end of the endoscope 2.

The endoscope system 1 includes: a first illuminating unit 41 and a second illuminating unit 42 that respectively emit illumination lights L1 and L2 toward biological tissue (subject) A from a distal end of the endoscope 2; an intensity-distribution changing unit 5 that changes an intensity distribution of the first illumination light L1 over time (see FIGS. 5A to 5E); an imaging unit 6 that images a first illumination image and a second illumination image of the biological tissue A being illuminated by the illumination lights L1 and L2; an image-processing unit 7 that creates a synthesized image by processing the second illumination image by using the first illumination image; and a display apparatus 8.

The first illuminating unit 41 has a first emitting surface 41a provided in a distal-end surface of the endoscope 2. The first illuminating unit 41 generates a single-wavelength first illumination light L1 that has a spatially non-uniform intensity distribution in a beam cross-section that is orthogonal to the optical axis, and emits the first illumination light L1 toward the biological tissue A from the first emitting surface 41a. The first illumination light L1 generally has an intensity gradient in which the brightness gradually decreases toward the periphery from the center of the light beam. Apart from such an overall intensity gradient in the beam cross-section, the first illumination light L1 has a dark/light pattern in which light portions having high intensities and dark portions having lower intensities than the light portions do, or no intensity, are periodically repeated in an alternating manner in the beam cross-section.

As shown in FIGS. 2A and 2B, the first illuminating unit 41 sequentially emits the two first illumination lights in which the spatial frequencies (periods X and Y of light portions and dark portion) of dark/light patterns differ from each other. A high-spatial-frequency first illumination light L1 has a period X that is smaller than a period Y of a low-spatial-frequency first illumination light L1.

The intensity-distribution changing unit 5 changes the intensity distribution of the first illumination lights L1 over time so that the light portions and the dark portions are exchanged with each other in a beam cross-section. By doing so, the light portions and the dark portions are sequentially projected in individual positions in the area on a surface B of the biological tissue A irradiated with the first illumination lights L1.

The second illuminating unit 42 has a second emitting surface 42a at a position in the distal-end surface of the endoscope 2 which is different from the position of the first emitting surface 41a. The second illuminating unit 42 emits, toward the biological tissue A from the second emitting surface 42a, a white second illumination light L2 having a spatially substantially uniform intensity distribution in a beam cross-section that is orthogonal to the optical axis. Such a second illuminating unit 42 includes a light source 42b provided in the main body 3, and a bundled fiber 42c and a projection lens 42d provided in the endoscope 2.

The light source 42b is, for example, a semiconductor light source such as an LED or an LD, or a lamp light source such as a xenon lamp. White light may be generated by combining red, green, and blue light output from a plurality of light sources. The white light output from the light source 42b is guided, by means of the bundled fiber 42c, to the projection lens 42d provided at the distal end of the endoscope 2, and is emitted via the projection lens 42d, in the form of a divergent light beam, from the second emitting surface 42a, which is the distal-end surface of the projection lens 42d.

The first illuminating unit 41 and the second illuminating unit 42 is controlled by a control apparatus (not shown) provided in the main body 3 so as to sequentially emit the high-spatial-frequency first illumination light L1, the low-spatial-frequency first illumination light L1, and the second illumination light L2 toward the biological tissue A.

FIGS. 3A to 3F show examples of the dark/light patterns of the intensity distribution of the first illumination light L1 and changes thereof over time. In FIGS. 3A to 3F, white regions represent light portions, and black regions represents dark portions.

The dark/light pattern in FIG. 3A is a checkered pattern in which square light portions and dark portions are alternately repeated in two directions that are orthogonal to each other.

Figure 3B:
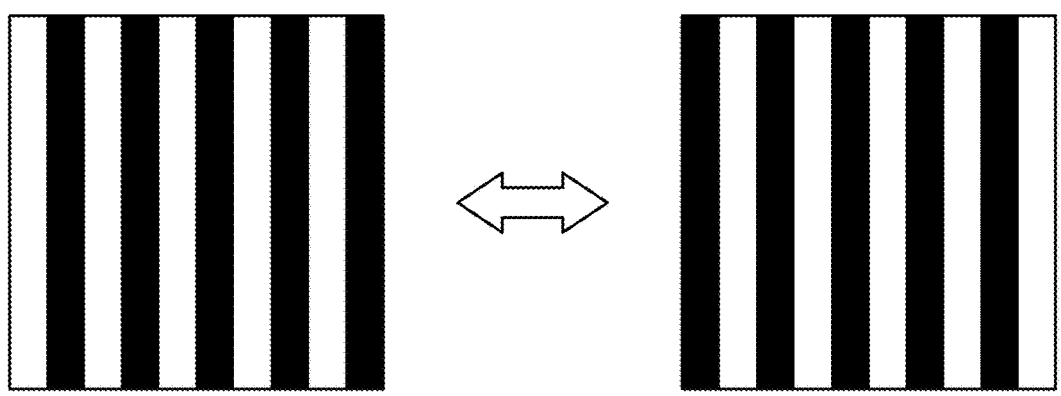
FIG. 3B is a diagram showing another example of the intensity distribution of the first illumination light and changes in the intensity pattern over time.
Figure 3C:
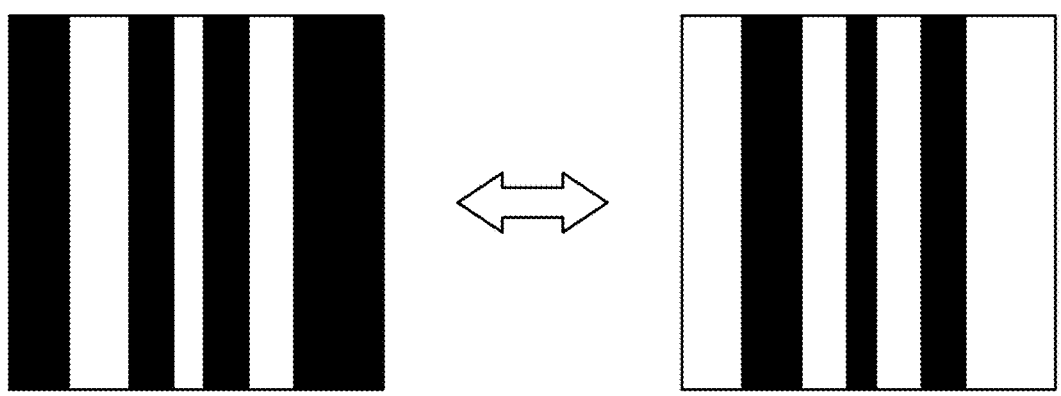
FIG. 3C is a diagram showing another example of the intensity distribution of the first illumination light and changes in the intensity pattern over time.

The dark/light patterns in FIGS. 3B and 3C are stripe shape in which straight band-like light portions and dark portions are alternately repeated only in the width direction that is orthogonal to the longitudinal directions of the light portions and the dark portions. In the stripe shape, the center intervals between the light portions and the dark portions may be constant, as shown in FIG. 3B, or may be different, as shown in FIG. 3C.

Figure 3D:
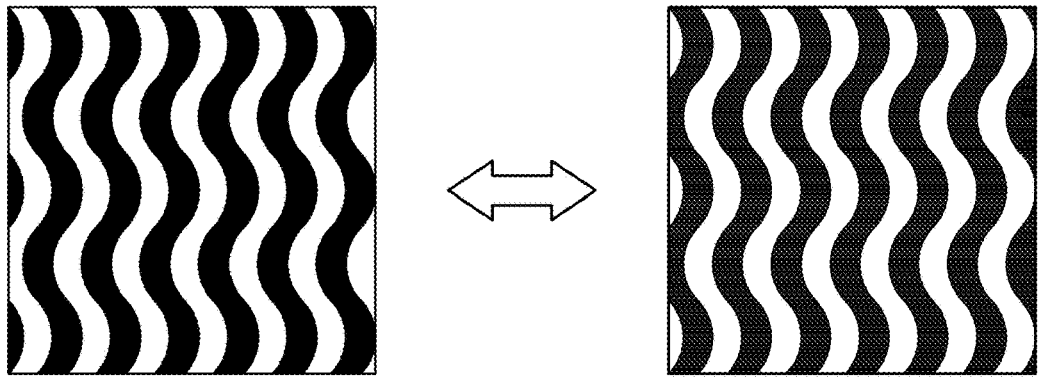
FIG. 3D is a diagram showing another example of the intensity distribution of the first illumination light and changes in the intensity pattern over time.

The dark/light pattern in FIG. 3D is a stripe shape in which wave-shaped band-like light portions and dark portions are alternately repeated only in the width direction that is orthogonal to the longitudinal directions of the light portions and dark portions.

Figure 3E:
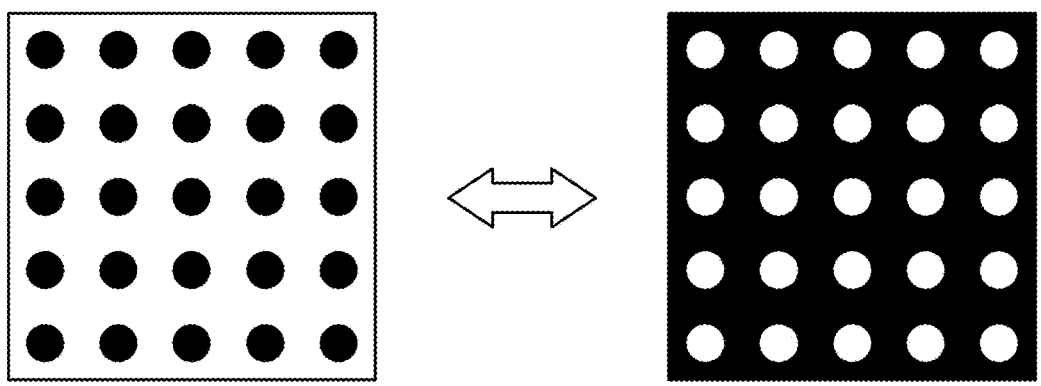
FIG. 3E is a diagram showing another example of the intensity distribution of the first illumination light and changes in the intensity pattern over time.

The dark/light pattern in FIG. 3E is a dot pattern in which, of the light portions and the dark portions, one is circles and the other is the background.

Figure 3F:
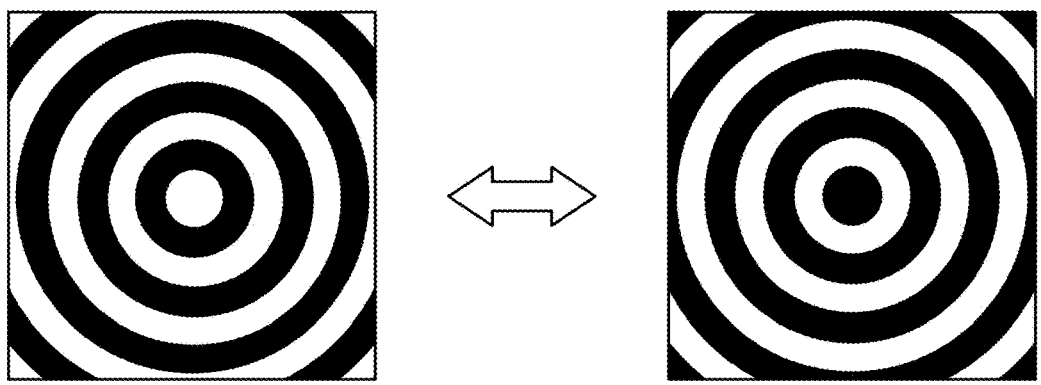
FIG. 3F is a diagram showing another example of the intensity distribution of the first illumination light and changes in the intensity pattern over time.

The dark/light pattern in FIG. 3F is a concentric pattern in which circular band-like light portions and dark portions are alternately repeated in the radial direction.

Figure 4A:
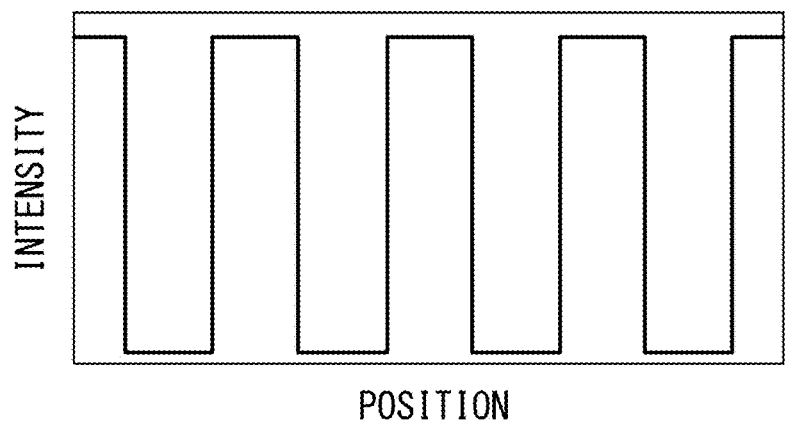
FIG. 4A is a diagram showing an example of the spatial profile of the intensity of the first illumination light.
Figure 4B:
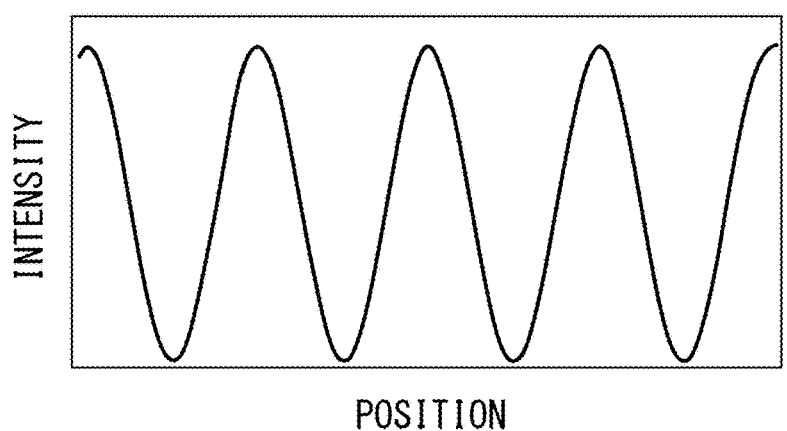
FIG. 4B is a diagram showing another example of the spatial profile of the intensity of the first illumination light.
Figure 4C:
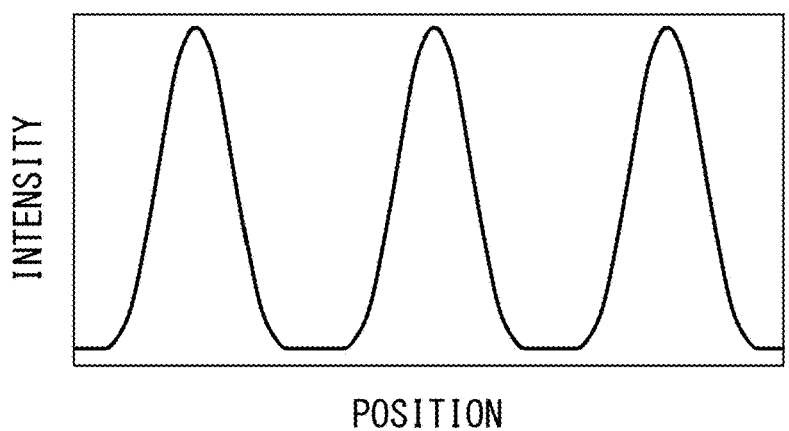
FIG. 4C is a diagram showing another example of the spatial profile of the intensity of the first illumination light.
Figure 4D:
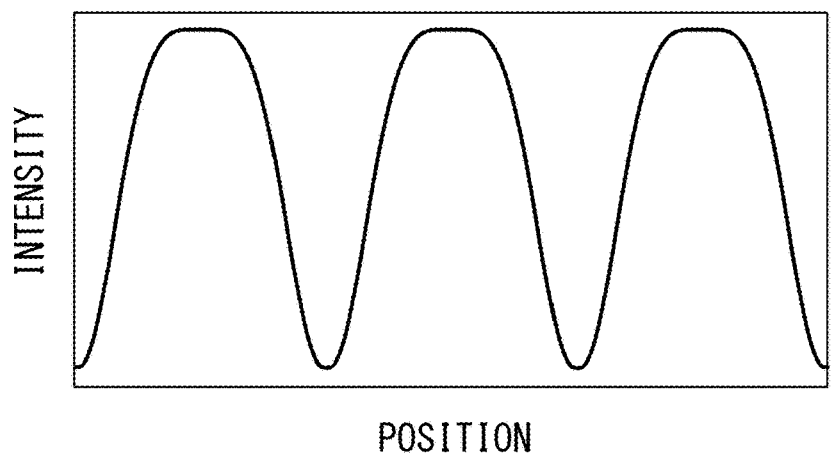
FIG. 4D is a diagram showing another example of the spatial profile of the intensity of the first illumination light.
Figure 4E:
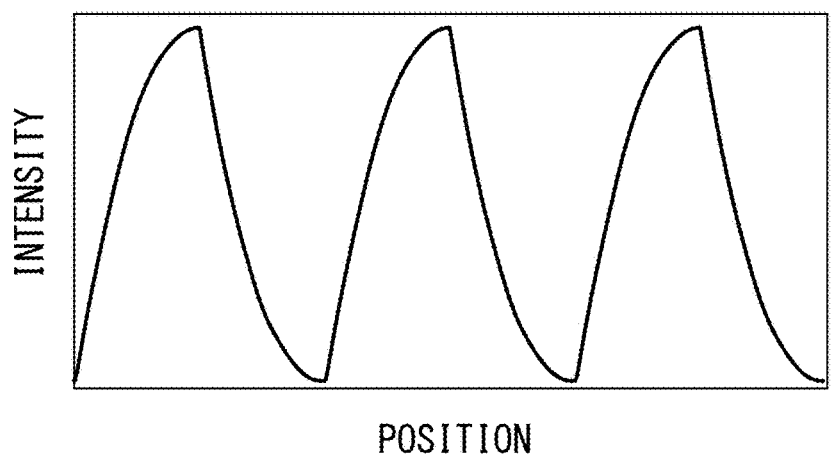
FIG. 4E is a diagram showing another example of the spatial profile of the intensity of the first illumination light.
Figure 4F:
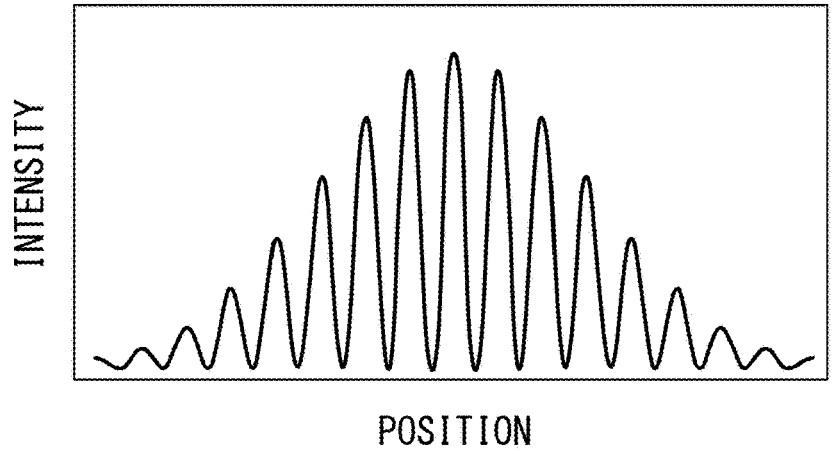
FIG. 4F is a diagram showing another example of the spatial profile of the intensity of the first illumination light.

FIGS. 4A to 4F show examples of intensity profiles representing spatial changes of the intensities between the light portions and the dark portions in the dark/light patterns in FIGS. 3A to 3F. An intensity profile may have a rectangular wave-shape, as shown in FIG. 4A, may be sinusoidal, as shown in FIG. 4B, may have an intermediate shape between a rectangular wave and a sine wave, as shown in FIGS. 4C and 4D, or may have an asymmetrical wave shape, as shown in FIG. 4E. In addition, in an intensity profile, the intensity may be the highest at the center of the first illumination light L1 and may decrease, as a whole, toward the periphery from the center, as shown in FIG. 4E.

FIGS. 5A to 5E, show configuration examples of the first illuminating unit 41 and the intensity-distribution changing unit 5.

Figure 5A:
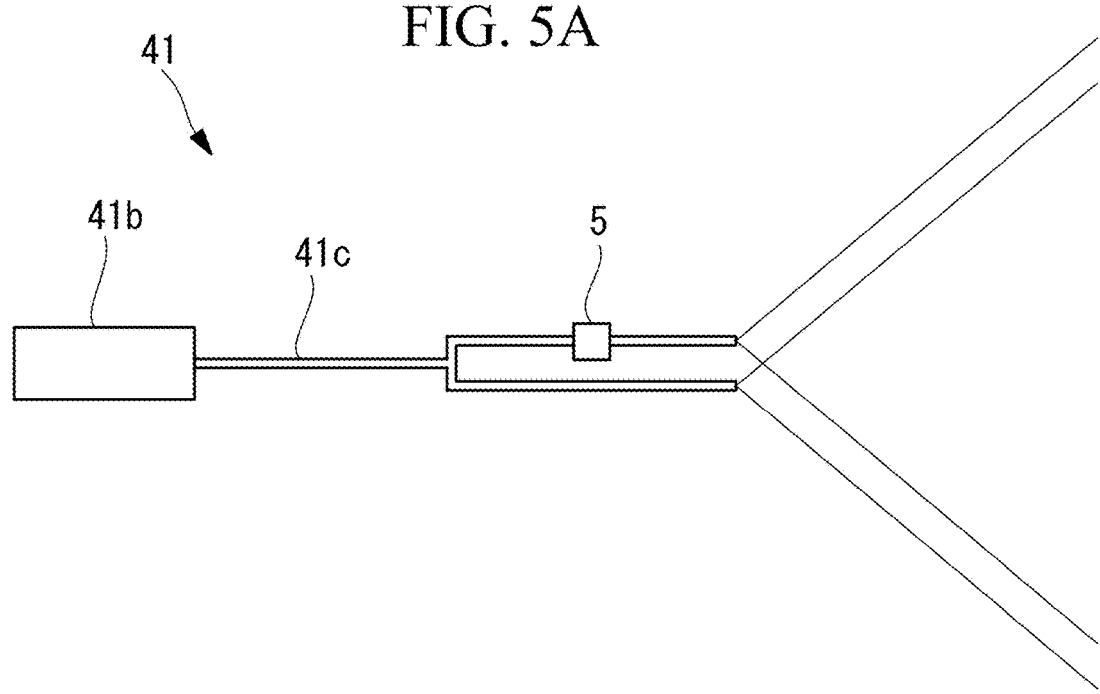
FIG. 5A is a diagram showing a configuration example of a first illuminating unit and an intensity-distribution changing unit.

The first illuminating unit 41 in FIG. 5A utilizes interference stripes of light as the dark/light pattern, and includes a laser light source 41b, and an optical path 41c via which two lights are output after the light output from the laser light source 41b is split into two. The optical path 41c is constituted of, for example, an optical fiber. As a result of the two lights emitted from the optical path 41c interfering with each other, the interference stripes having a sinusoidal intensity profile are generated so as to serve as the dark/light pattern, as shown in FIG. 5B.

Figure 5B:
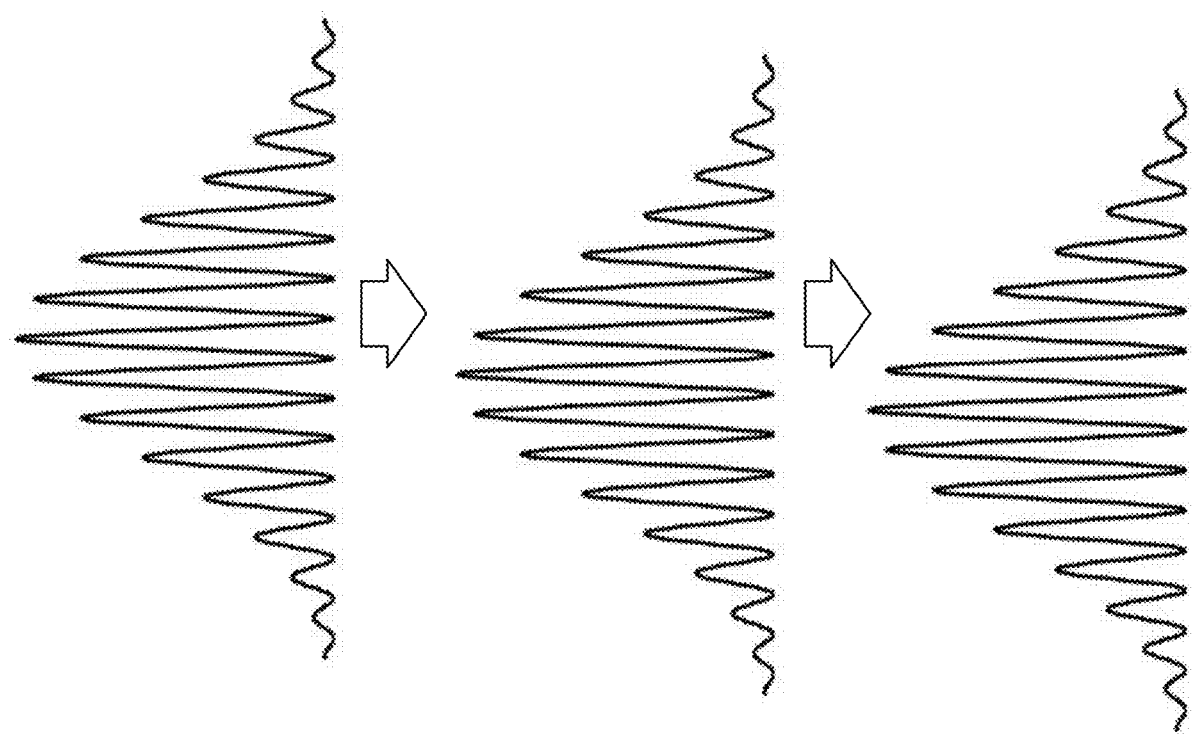
FIG. 5B is a diagram for explaining a dark/light pattern generated by the first illumination unit in FIG. 5A and changes in the dark/light pattern over time.

As a result of changing the length of the optical path of one of the two split light, the intensity-distribution changing unit 5 changes the positions of the interference stripes in a direction that is orthogonal to the optical axis of the illumination light, as shown in FIG. 5B. Therefore, the intensity-distribution changing unit 5 includes an optical device that is provided in the optical path of one of the two lights and that changes the length of the optical path.

Figure 5C:
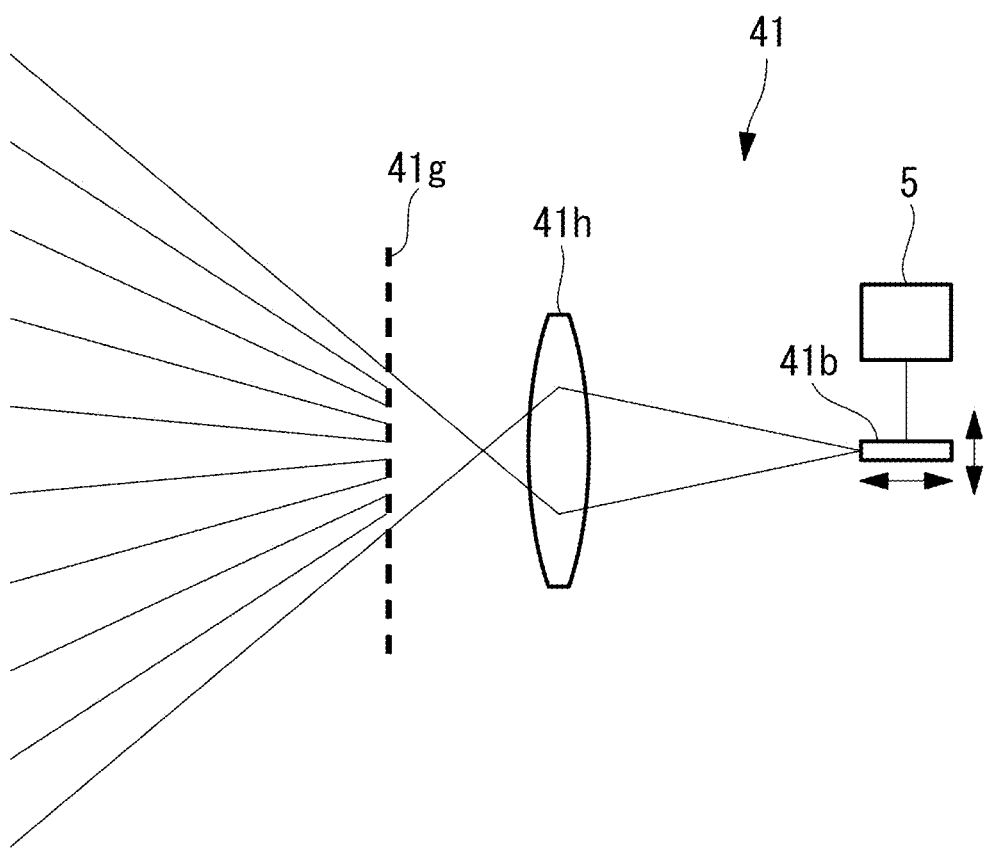
FIG. 5C is a diagram showing another configuration example of a first illuminating unit and an intensity-distribution changing unit.

The first illuminating unit 41 in FIG. 5C forms a dark/light pattern on the surface B of the biological tissue A in a manner similar to forming a shadowgram, and includes the laser light source 41b and a mask 41g provided in the distal-end portion of the endoscope 2. Instead of the laser light source 41b, other types of light sources, such as an LED, may be employed, or an optical fiber that guides light from a light-source apparatus disposed outside the endoscope 2 to the distal-end portion of the endoscope 2 may be employed.

The mask 41g has a translucent region through which laser light is allowed to pass and a light-blocking region that blocks the laser light, and the translucent region and the light-blocking region form a projection pattern corresponding to the dark/light pattern. Such a mask 41g is constituted of, for example, a light-blocking substrate in which openings are formed so as to serve as the translucent regions or a transparent substrate in which a light-blocking film that serves as the light-blocking regions is formed. As a result of passing through the mask 41g, the laser light output from the laser light source 41b is transformed into the first illumination light L1 having the dark/light pattern. A lens 41h that changes the divergence angle of the laser light so that the first illumination light L1 radiated onto the biological tissue A has a desired divergence angle may be provided between the laser light source 41b and the mask 41g.

It is possible to change the spatial frequency of the first illumination light L1 emitted from the mask 41g by changing the interval between the laser light source 41b and the mask 41g in the optical-axis direction by moving the laser light source 41b and the mask 41g relative to each other. Therefore, an actuator that moves the laser light source 41b and the mask 41g relative to each other in the optical-axis direction is provided. With an increase in the interval between the laser light source 41b and the mask 41g, the spatial frequency of the first illumination light L1 is increased.

As a result of moving the laser light source 41b and the mask 41g relative to each other in the direction that intersects the optical axis of the laser light, the intensity-distribution changing unit 5 changes the intensity distribution over time. Therefore, the intensity-distribution changing unit 5 includes an actuator that moves the laser light source 41b and the mask 41g relative to each other in the direction that intersects the optical axis. Such an intensity-distribution changing unit 5 is suitable for the striped dark/light patterns in FIGS. 3B to 3D by making it possible to change the intensity distribution over time by moving the laser light source 41b and the mask 41g relative to each other only in the width direction that is orthogonal to the longitudinal directions of the light portions and the dark portions.

The first illuminating unit 41 in FIG. 5D includes the laser light source 41b and a mask 41i provided in the main body 3 and an image-guiding fiber 41j provided in the endoscope 2.

The laser light output from the laser light source 41b is focused by a reflector 41d and illuminates the mask 41i. The mask 41i is a liquid-crystal device that can electrically control the light transmittance at individual positions in an incident region in which the laser light is made incident, and has a dark/light pattern, as with the mask 41g. The image of the mask 41i is formed at an incident end surface of the image-guiding fiber 41j by the focusing lens 41k, is guided to a projection lens 41e at the distal end of the endoscope 2 by the image-guiding fiber 41j, while retaining the dark/light pattern, and is emitted from the projection lens 41e.

A control device that controls the light transmittance at the individual positions in the incident region of the laser light is connected to the mask 41i. The mask 41i, which is constituted of a liquid-crystal device, can form an arbitrary projection pattern and can freely change the arbitrary projection pattern over time. Specifically, the intensity-distribution changing unit 5 is constituted of a control device. The spatial frequency of the first illumination light L1 is changed by means of the control device performing electrical control of the liquid-crystal device.

The first illuminating unit 41 in FIG. 5E includes a light-source array 411 and a light-guiding member 41m that guides light while retaining the incident angle of the light with respect to the optical axis thereof. The light-source array 411 has a plurality of laser light sources 41b that are arrayed so that incident angles of the light are different from each other with respect to the incident end of the light-guiding member 41m. Although the plurality of laser light sources 41b are arrayed in a single row in FIG. 5E, the plurality of laser light sources 41b may be two-dimensionally arrayed. The light-guiding member 41m is, for example, a rod lens or a multimode fiber.

The laser light emitted from the laser light source 41b is converted to a parallel light beam by a lens 41n, and is made incident on an incident end of the light-guiding member 41m. The laser light that has entered the light-guiding member 41m is guided via the interior of the light-guiding member 41m while retaining the angle thereof, and is emitted toward the biological tissue A from an emitting end of the light-guiding member 41m at the same angle as the incident angle with respect to the incident end. Because the laser light is spread out in the circumferential direction as a result of being repeatedly reflected in the light-guiding member 41m, the light emitted from the light-guiding member 41m takes an annular shape. Therefore, as a result of a plurality of laser light sources 41b being simultaneously turned on, the first illumination light L1 having a concentric pattern shown in FIG. 3F is generated.

A control device that controls turning on/off of the individual laser light sources 41b is connected to the light-source array 411. The spatial frequency of the first illumination light L1 is changed in accordance with the intervals between the plurality of laser light sources 41b to be turned off by the control device. The intensity-distribution changing unit 5 changes the intensity distribution by changing the laser light sources 41b to be turned on by the control device.

The first illuminating unit 41 in FIGS. 5A to 5E may change the spatial frequency of the first illumination light L1 by expanding/contracting the dark/light pattern projected onto the biological tissue A by means of a zoom lens disposed on the optical path of the first illumination light L1.

The imaging unit 6 includes an imaging lens 6a that is provided at the distal end of the endoscope 2 and that focuses the light coming from the biological tissue A, and an imaging device 6b that captures an image of the biological tissue A formed by the imaging lens 6a.

The imaging device 6b possesses sensitivity for both the single-color first illumination light L1 and the white second illumination light L2. In the case in which the first illumination light L1 is light in a wavelength band other than the visible range, an imaging device 6b including a filter array consisting of red, green, and blue color filters for the second illumination light L2 and a color filter for the first illumination light L1 is employed.

In the case in which the first illumination light L1 is near-infrared light or infrared light, a laminated-type imaging device 6b in which a substrate having an RGB sensor formed therein and a substrate having a near-infrared-light or infrared-light sensor formed therein are laminated may be used. Alternatively, in addition to the imaging device 6b for white light, another imaging device for near-infrared light or infrared light may be included, and the near-infrared light or the infrared light may be separated between the imaging lens 6a and the imaging device 6b and deflected toward the imaging device. In the case in which the near-infrared or infrared first illumination light L1 is used in this way, the first illumination image and the second illumination image may be simultaneously imaged by simultaneously irradiating the biological tissue A with the first illumination light L1 and the second illumination light L2.

The imaging unit 6 images two first illumination images, which are treated as one set, by executing image-capturing twice when the high-spatial-frequency first illumination light L1 is radiated onto the biological tissue A, images two first illumination images, which are treated as one set, by executing image-capturing twice when the low-spatial-frequency first illumination light L1 is radiated onto the biological tissue A, and images one second illumination image by executing image-capturing once when the second illumination light L2 is radiated onto the biological tissue A. In other words, four first illumination images and one second illumination image are imaged. Therefore, the operations of the illuminating units 41 and 42 and the imaging device 6b are controlled by the control apparatus so that the timing at which the illumination lights L1 and L2 are emitted from the illuminating units 41 and 42 and the timing at which the images are captured by the imaging device 6b are synchronized with each other. The two sets of the first illumination images and the second illumination image imaged by the imaging device 6b are transmitted to the image-processing unit 7 from the imaging device 6b.

Figure 6:
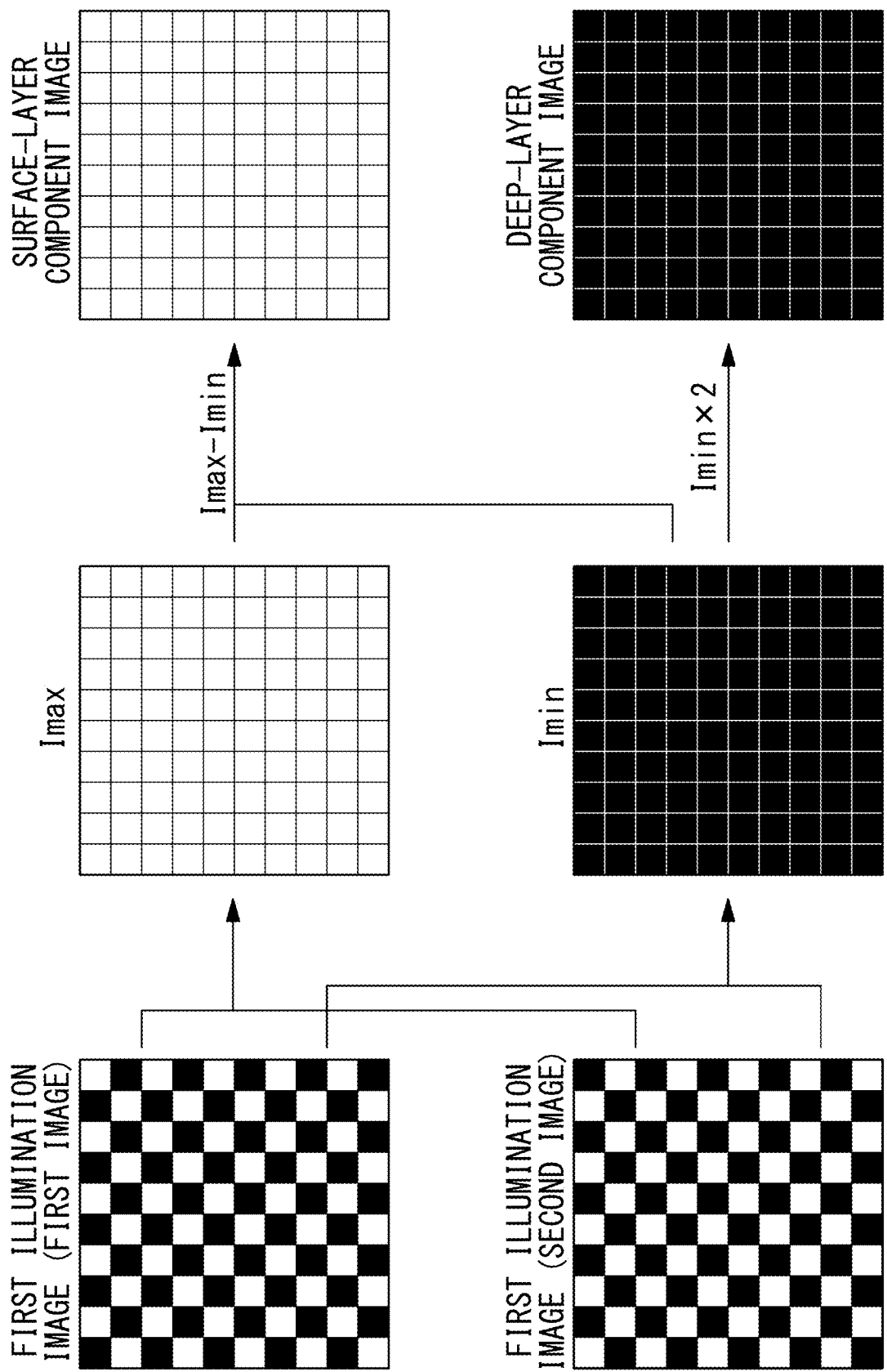
FIG. 6 is a diagram for explaining processing for creating, in a separating-processing unit, a surface-layer component image and a deep-layer component image from one set of first illumination images.

The intensity distributions of the high-spatial-frequency and low-spatial-frequency first illumination lights L1 are changed over time by the intensity-distribution changing unit 5, as shown in FIGS. 3A to 3F. By executing image-capturing at two times at which the high-spatial-frequency first illumination light L1 having the light portions and the dark portions inverted with respect to each other is radiated onto the biological tissue A, the imaging device 6b images two first illumination images which are treated as one set and in which the projection regions of the light portions and the projection regions of the dark portions are inverted with respect to each other, the projection regions of the light portions complement each other, and the projection regions of the dark portions complement each other, as shown in FIG. 6. Similarly, by executing image-capturing at two times at which the low-spatial-frequency first illumination light L1 having the light portions and the dark portions inverted with respect to each other is radiated onto the biological tissue A, the imaging device 6b images two first illumination images which are treated as one set. In the one set of first illumination images in FIG. 6, the white regions represent the projection regions of the light portions, and the black regions represent the projection regions of the dark portions. Therefore, the operations of the intensity-distribution changing unit 5 and the imaging device 6b are controlled by the control apparatus so that the timing at which the intensity distribution is changed by the intensity-distribution changing unit 5 and the timing at which images are captured by the imaging device 6b are synchronized with each other.

The image-processing unit 7 includes a separating-processing unit 71 that separates three images showing different depths of the biological tissue A from the four first illumination images, and an image-synthesizing unit 72 that processes the second illumination image by using images other than the image information about the outermost surface side of the biological tissue A among the separated three of image information.

Figure 7:
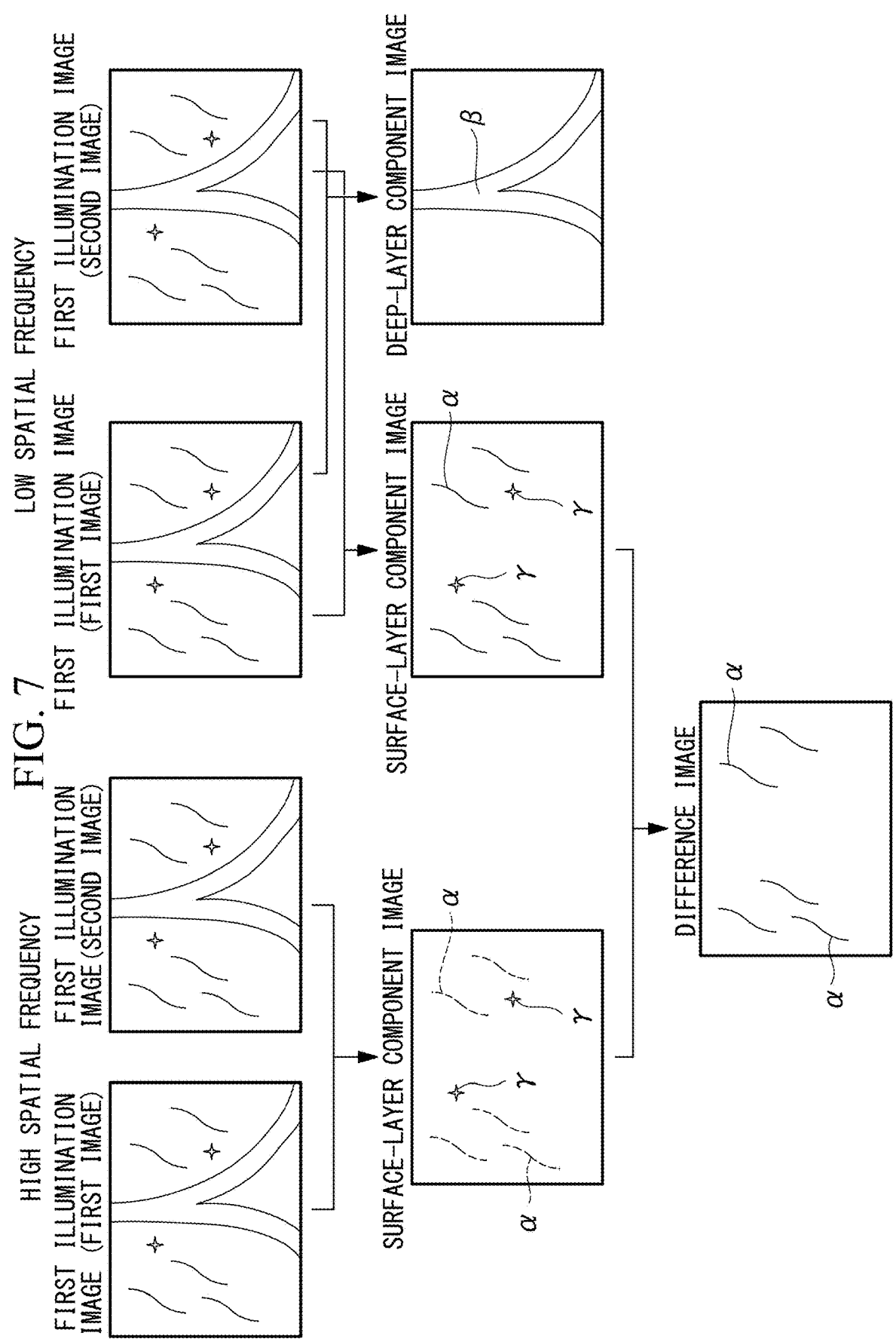
FIG. 7 is a diagram for explaining processing for creating, in the separating-processing unit, a difference image from two sets of first illumination images.

FIGS. 6 and 7 show the image processing performed by the separating-processing unit 71. With regard to pixels at the individual positions of the one set of first illumination images, intensity values Imax when the light portions are projected and intensity values Imin when the dark portions are projected are imaged. The separating-processing unit 71 creates, from the intensity values Imin of the one set of first illumination images, a deep-layer component image that contains a large amount of information about a deep layer D of the biological tissue A, and creates, from the intensity values Imin and the intensity values Imax of the one set of first illumination images, a surface-layer component image that contains a large amount of information about the surface B and a surface layer C of the biological tissue A.

Figure 8:
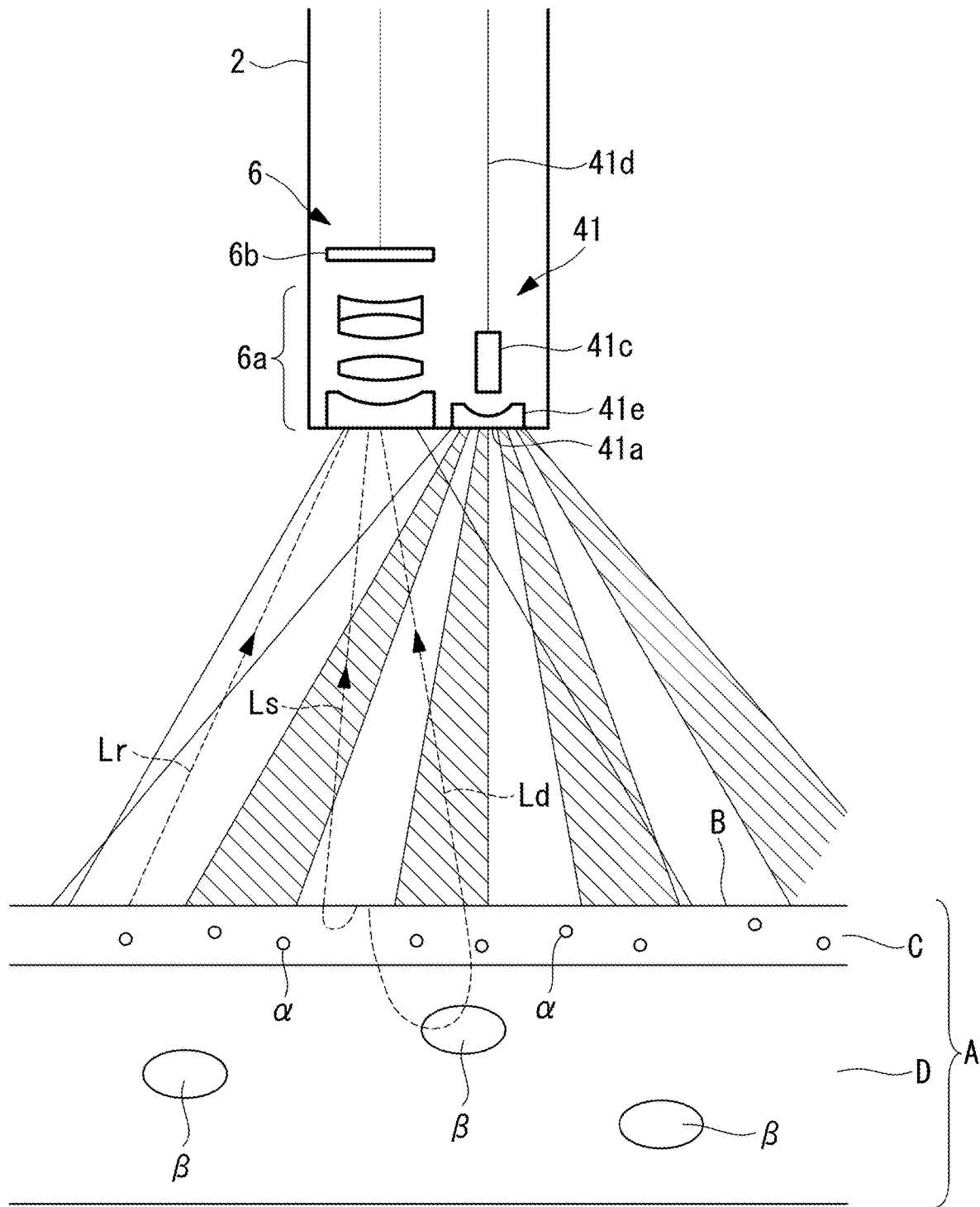
FIG. 8 is a diagram for explaining the relationship between a specular light, a surface scattered light, and an internal scattered light generated in biological tissue due to irradiation thereof with the first illumination light and the positions at which these light are generated.

The biological tissue A is a scattering body, and contains, as shown in FIG. 8, structures α, such as capillaries, in the surface layer C up to several tens of micrometers from the surface B and structures β, such as thick blood vessels, in the deep layer D that is deeper than the surface layer C. When the first illumination light L1 having the dark/light pattern is radiated onto the biological tissue A, a specularly reflected (specular) light Lr, a surface scattered light Ls, and an internal scattered light Ld are generated in the biological tissue A.

The specular light Lr is reflected light of the first illumination light L1 that is specularly reflected at the surface B of the biological tissue A, and is generated in the projection regions of the light portions.

The surface scattered light Ls is scattered light of the first illumination light L1 that has entered the biological tissue A from the projection regions of the light portions, that has passed through the surface layer C while repeatedly being scattered, and that has been emitted from the surface B. Most of the surface scattered light Ls is emitted from the projection regions of the light portions.

The internal scattered light Ld is scattered light of the first illumination light L1 that has entered the biological tissue A from the projection regions of the light portions, that has passed through the surface layer D while repeatedly being scattered, and that has been emitted from the surface B. A portion of the internal scattered light Ld is emitted from the projection regions of the light portions, and the rest is propagated to the projection regions of the dark portions and is emitted from the projection regions of the dark portions.

In this way, the intensity values Imin of the projection regions of the dark portions in the one set of first illumination images are mainly based on the internal scattered light Ld, and mainly contain information about the deep layer D. On the other hand, the intensity values Imax of the projection regions of the light portions in the one set of first illumination images are based on the specular light Lr, the surface scattered light Ls, and the internal scattered light Ld, and contain information about the surface B, the surface layer C, and the deep layer D.

Figure 9:
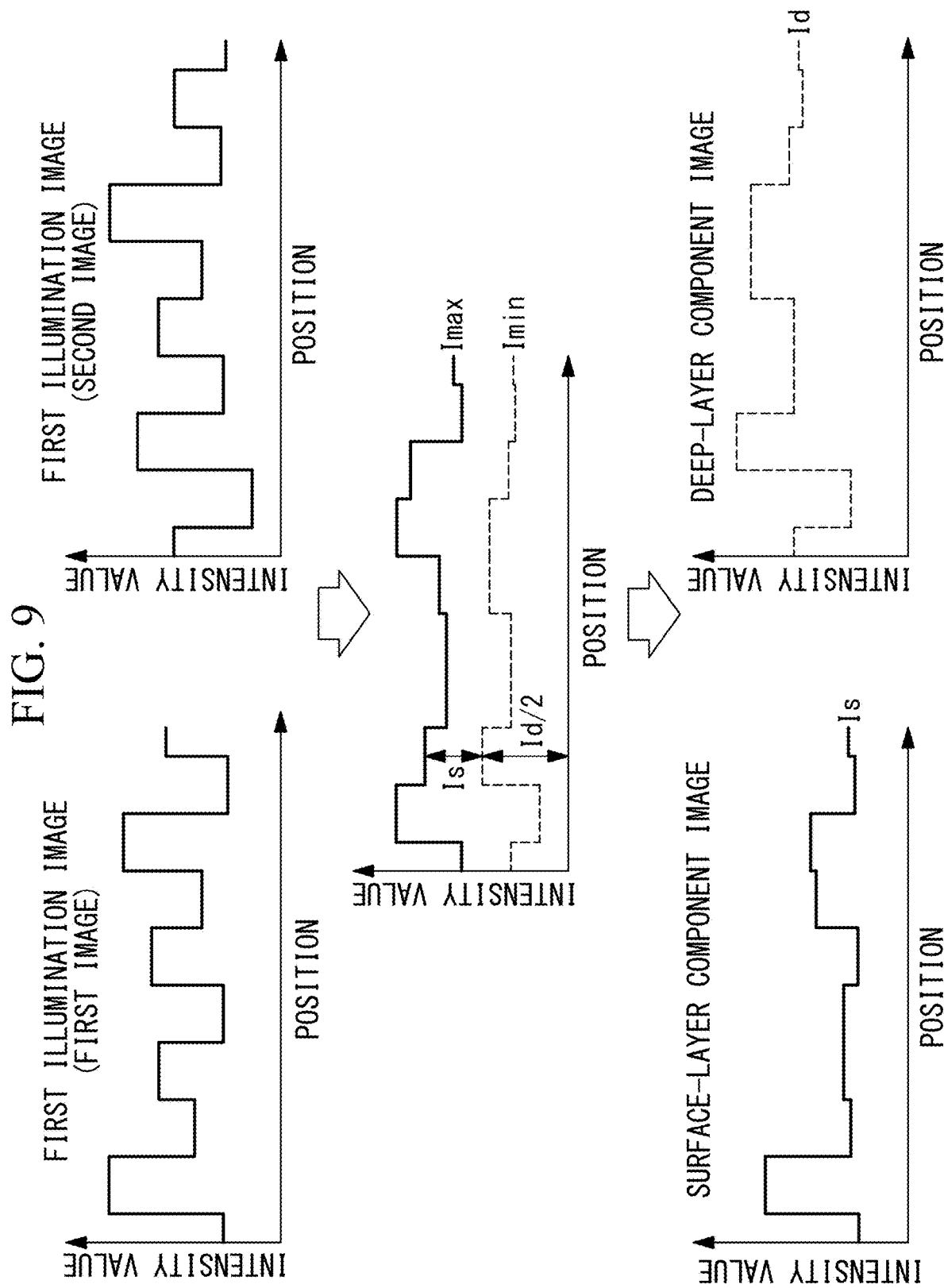
FIG. 9 is a diagram for explaining a method for creating a separated image in the separating-processing unit.

FIG. 9 shows a specific method for creating the surface-layer component image and the deep-layer component image by means of the separating-processing unit 71. As shown in FIG. 9, the one set of first illumination images have brightness distributions in which the intensity values increase in pixels corresponding to the projection regions of the light portions and the intensity values decrease in the pixels corresponding to the projection regions of the dark portions. FIG. 9 shows, in order to simply the description, an intensity profile for the case in which the first illumination light L1 has a dark/light pattern in which the light portions and the dark portions are repeated at equal intervals, as in the dark/light pattern in FIG. 3A or 3B, and boundaries between the pixels in the image and the boundaries of the light portions and dark portions in the dark/light pattern coincide with each other (in other words, one light portion or dark portion corresponds to one pixel).

As has been described above, from the one set of first illumination images, two intensity values Imax and Imin are imaged for the respective pixels. With regard to the respective pixels, the separating-processing unit 71 sets the grater one of the intensity values to be the intensity value Imax and the lower one of the intensity values to be the intensity value Imin. Next, the separating-processing unit 71 calculates intensity values Is of the respective pixels of the surface-layer component image and intensity values Id of the pixels of the deep-layer component image from the following expressions, and creates a surface-layer component image having the intensity values Is and a deep-layer component image having the intensity values Id:

$$Is = Imax - Imin; \text{ and}$$

$$Id = Imin \times 2.$$

By doing so, a deep-layer component image that has the intensity values Imin mainly containing the information about the deep layer D is created. The information about the deep layer D is removed by subtracting the intensity values Imin from the intensity values Imax, and thus, a surface-layer component image having the intensity values Is mainly containing the information about the surface B and the surface layer C is created.

In general, with an increase in the wavelength, light is less likely to be scattered by a scattering body and reaches deeper positions of the biological tissue A; therefore, with an increase in the wavelength of the first illumination light L1, the internal scattered light Ld contains more information about the deeper positions. Therefore, by using a near-infrared or infrared first illumination light L1, it is possible to obtain a deep-layer component image containing information about deeper positions. So that it is possible to change the depths of the information contained in the deep-layer component image, the first illuminating unit 41 may be capable of selecting the wavelength of the first illumination light L1 from a plurality of wavelengths.

Here, a boundary between the depth of the information contained in the surface-layer component image and the depth of the information contained in the deep-layer component image is determined in accordance with the interval between the light portions and the dark portions on the surface B of the biological tissue A, and the boundary is set at a shallower position with a decrease in the interval between the light portions and the dark portions. Therefore, the surface-layer component image (first surface layer image information) based on the high-spatial-frequency first illumination light L1 mainly contains information about the surface B, as shown in FIG. 2A. As opposed to this, the surface-layer component image (second surface layer image information) based on the low-spatial-frequency first illumination light L1 contains information about both the specular light Lr at the surface B and the internal scattered light Ld at the surface layer C, as shown in FIG. 2B.

FIG. 7 shows the process of obtaining a difference image from the four first illumination images of the biological tissue A illuminated by the high-spatial-frequency and low-spatial-frequency first illumination lights L1. As shown in FIG. 7, the respective first illumination images contain the structures α, such as capillaries in the surface layer C, and the structures β, such as thick blood vessels in the deep layer D, and, furthermore, a specular light γ originating from the first illumination light L1 appears in said images. The surface-layer component image based on the low-spatial-frequency first illumination light L1 and the surface-layer component image based on the high-spatial-frequency first illumination light L1, which are generated from such first illumination images, both contain the structures α in the surface layer C and the specular light γ. The separating-processing unit 71 removes a specular light Lr (see reference sign γ in FIG. 7) in the surface B by subtracting the surface-layer component image (first surface layer image information) obtained by using the high-spatial-frequency first illumination light L1 from the surface-layer component image (second surface layer image information) obtained by using the low-spatial-frequency first illumination light L1, and thus, creates a difference image (difference image information) that mainly contains the information about the surface layer C.

Figure 10:
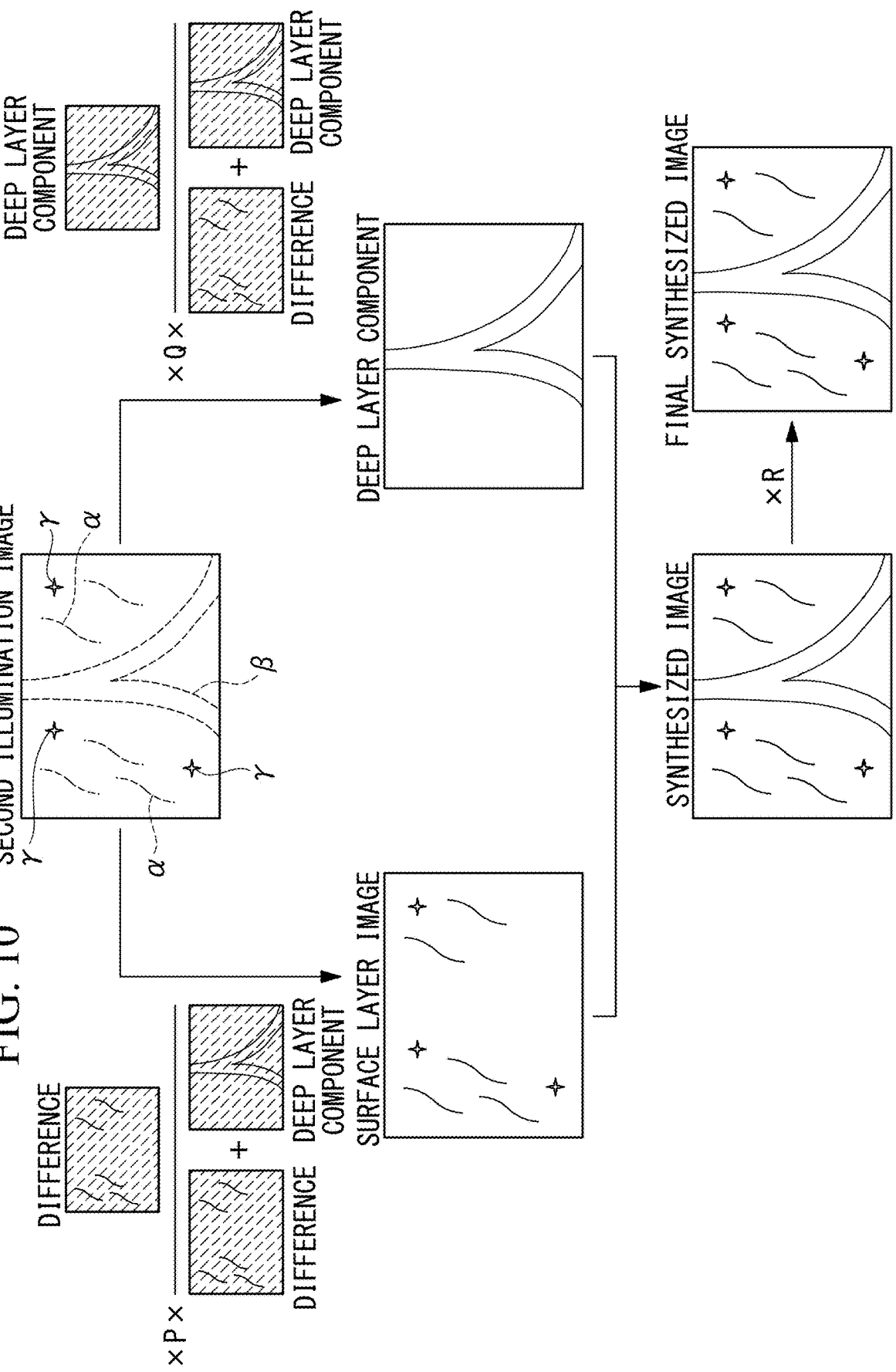
FIG. 10 is a diagram for explaining processing for creating, in an image-synthesizing unit, a synthesized image and a final synthesized image from a second illumination image.

FIG. 10 shows the image processing performed by the image-synthesizing unit 72. The image-synthesizing unit 72 processes the second illumination image by using two of information, namely, the difference image information (difference image) shown in FIG. 7 and the deep layer image information (deep-layer component image) based on the low-spatial-frequency first illumination light L1. Specifically, as shown in FIG. 10, the image-synthesizing unit 72 creates a surface layer image on the basis of expression (a) below and a deep layer image on the basis of expression (b) below:

Surface layer image=second illumination image×$P$×
difference image information/(difference image
information+deep layer image information)     (a); and Deep layer image=second illumination image×$Q$×
deep layer image information/(difference image
information+deep layer image information)     (b).

In other words, the image-synthesizing unit 72 calculates a ratio of the difference image with respect to the sum of the difference image information and deep-layer image information, and creates a surface-layer image by multiplying the second illumination image by the calculated ratio. The image-synthesizing unit 72 calculates a ratio of the deep-layer image information with respect to the sum of the difference image information and the deep layer image information, and creates a deep-layer image by multiplying the second illumination image by the calculated ratio. P in expression (a) is a coefficient for emphasizing the information about the surface layer in the synthesized image, and Q in expression (b) is a coefficient for emphasizing the information about the deep layer in the synthesized image. The coefficients P and Q are set, for example, by a user via an input means (not shown) connected to the main body 3.

Next, the image-synthesizing unit 72 creates a synthesized image by adding the surface-layer image and the deep-layer image. It is possible to create a synthesized image in which, in accordance with the above-described coefficients P and Q, one of the information about the surface layer C and the information about the deep layer D is emphasized while retaining both the information about the surface layer C and the information about the deep layer D. Specifically, a synthesized image in which the information about the surface layer C is emphasized is obtained by increasing the coefficient P, and a synthesized image in which the information about the deep layer D is emphasized is obtained by increasing the coefficient Q. Similarly, by setting one of the above-described coefficients P and Q to be low, it is possible to create a synthesized image in which one of the information about the surface layer C and the information about the deep layer D is suppressed while retaining both the information about the surface layer C and the information about the deep layer D.

The image-synthesizing unit 72 may create a final synthesized image in which the brightness thereof is adjusted so as to be equivalent to the second illumination image by multiplying the synthesized image (=surface-layer image+deep-layer image) by a coefficient R, as in expression (c) below:

final synthesized image=$R$×(surface-layer image+
deep-layer image)     (c).

Such an image-processing unit 7 is realized, for example, in the form of an image-processing program executed by a computer. In other words, a central processing unit (CPU), a main storage apparatus, such as a RAM, and an auxiliary storage apparatus, such as a hard disk drive, are built into the main body 3, and an image-processing program for causing the CPU to execute the above-described processing by means of the image-processing unit 7 is stored in the auxiliary storage apparatus. The image-processing program is loaded into the main storage apparatus from the auxiliary storage apparatus, the CPU executes the processing in accordance with the image-processing program, and, as a result, the above-described function of the image-processing unit 7 is realized.

The display apparatus 8 includes a display unit 81 that displays an image created by the image-processing unit 7 and a display-switching unit 82 that switches the image to be displayed on the display unit 81 between the second illumination image and the final synthesized image.

The display-switching unit 82 is configured, for example, so that the user can select one of the second illumination image and the final synthesized image by using an input means (not shown). As a result of transmitting the second illumination image or the final synthesized image to the display apparatus 8 from the image-processing unit 7 in response to the selection result of the display-switching unit 82, the selected image is displayed on the display unit 81.

When the second illumination light L2, which is normal white light having an intensity distribution that is spatially substantially uniform, is radiated onto the biological tissue A, the specular light Lr, the surface scattered light Ls, and the internal scattered light Ld are made incident on the imaging unit 6 in a state in which these light beams are superimposed on each other. Such a second illumination image, which is a normal white-light image, contains the structures α in the surface layer C, the structures β in the deep layer D, and the specular light γ originating from the second illumination light, as shown in FIG. 10.

In contrast, when the first illumination light L1 having a dark/light pattern is radiated onto the biological tissue A, the internal scattered light Ld containing a large amount of the information about the deep layer D is spatially separated from the specular light Lr and the surface scattered light Ls that contains information about the surface B and the surface layer C. Then, it is possible to create a surface-layer component image that contains the information about the surface B, the surface layer C, and the deep layer D on the basis of the light portions of the first illumination image, and to create a deep-layer component image that contains the information about the deep layer D on the basis of the dark portions of the first illumination image. By using such a surface-layer component image and deep-layer image information, it is possible to create, from the second illumination image, a surface layer image, which mainly contains the information about the surface B and the surface layer C, and a deep-layer image, which mainly contains the information about the deep layer D, and it is possible to reconstruct, from the surface layer image and the deep-layer image, a synthesized image which is a white-light image of the biological tissue A having enhanced visibility of the structures α in the surface layer C and the structures β in the deep layer D.

Here, due to the fact that the positions of the first emitting surface 41a and the second emitting surface 42a differ from each other, a specular light based on the first illumination light L1 and a specular light based on the second illumination light L2 are generated at positions that are different from each other. Because of this, the position of the specular light γ of the first illumination image and the position of the specular light γ of the second illumination image are displaced from each other.

Figure 13:
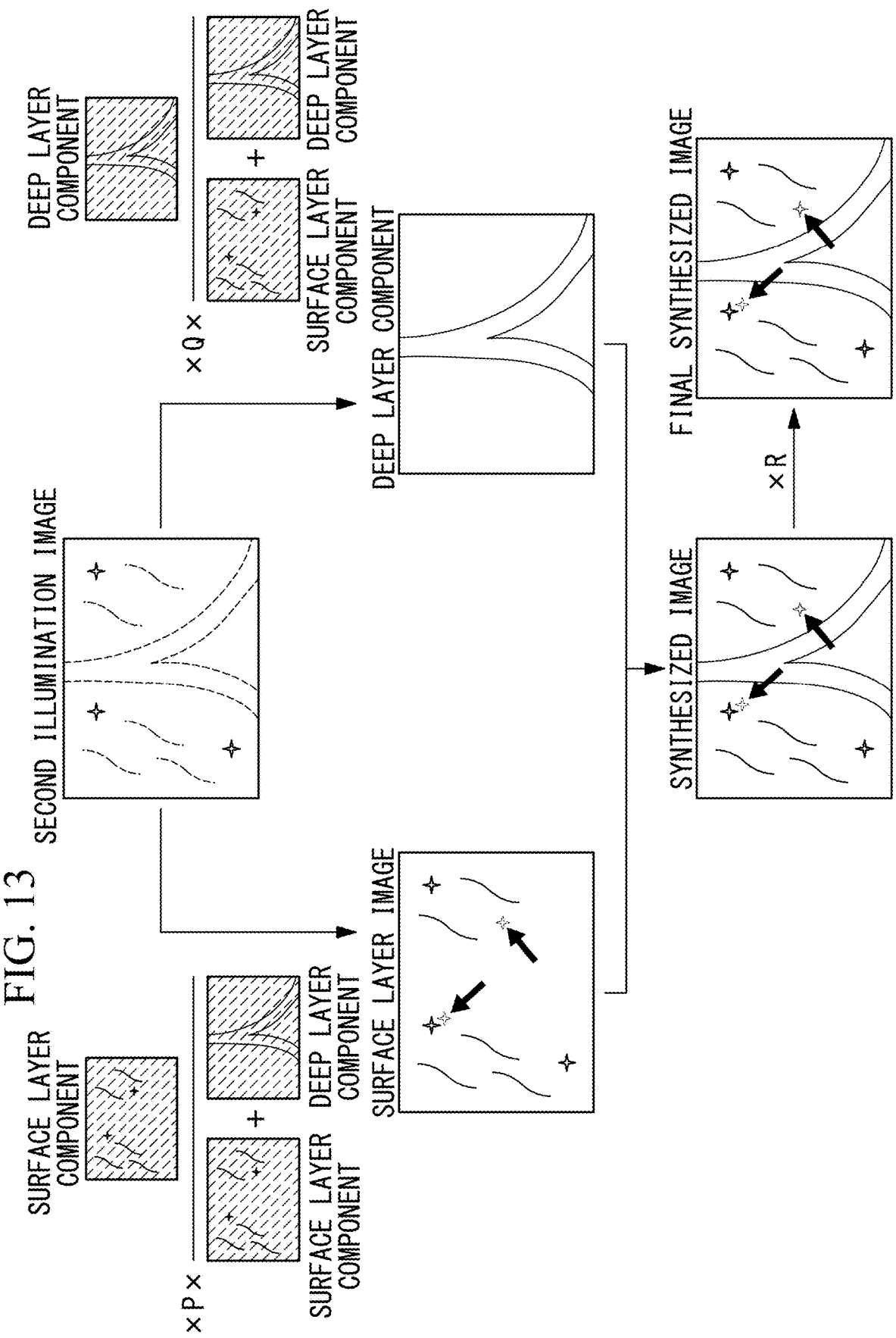
FIG. 13 is a diagram for explaining processing for creating a synthesized image and a final synthesized image in a Comparative Example of the present invention.

As shown in FIG. 13, which is a comparative example, in the case in which a surface-layer component image of a high-spatial-frequency or low-spatial-frequency first illumination image is used in creating the surface-layer image instead of the difference image, noise originating from the specular light in the first illumination image at a position that is different from that of the specular light in the second illumination image occurs in the synthesized image and the final synthesized image (see filled arrow in the figure).

In contrast, with this embodiment, a surface-layer component image in which the information about the surface B is dominant is obtained by using a high-spatial-frequency first illumination light, the specular light is removed by using this surface-layer component image, and thus, the difference image containing the information about the surface layer C is obtained. By using such a difference image, there is an advantage in that it is possible to obtain a natural synthesized image in which the structures α in the surface layer C and the structures β in the deep layer D are emphasized while suppressing the occurrence of the noise originating from the specular light in the first illumination image.

In order to obtain the synthesized image and final synthesized image from which the specular light is precisely removed, it is preferable that the periods X of the light portions and the dark portions of the high-spatial-frequency first illumination light L1 on the surface B (see FIG. 2A) satisfy conditional expression (1) below:

$$0.005\ \text{mm} < X < 2.0\ \text{mm} \quad (1).$$

As a result of the period X satisfying conditional expression (1), it is possible to obtain a surface-layer component image that contains almost no other information but the information about the surface B. In the case in which the period X is equal to or less than 0.005 mm, the proportion of the internal scattered light Ld emitted from the projection regions of the dark portions increases, and the differences between the intensity values Imax and the intensity values Imin consequently decrease, and thus, the information about the surface B contained in the surface-layer component image may become insufficient. On the other hand, in the case in which the period X is equal to or greater than 2.0 mm, the proportion of the information about the surface layer C contained in the surface-layer component image increases, and it becomes difficult to selectively remove only the specular light in the difference image.

In order to precisely separate the information about the surface layer C and the information about the deep layer D from each other, it is preferable that the periods Y of the light portions and the dark portions of the low-spatial-frequency first illumination light L1 on the surface B (see FIG. 2B) satisfy conditional expression (2) below:

$$0.1\ \text{mm} < Y < 50\ \text{mm} \quad (2).$$

As a result of the period Y satisfying conditional expression (2), it is possible to obtain a surface-layer component image containing abundant information about the surface layer C and a deep-layer component image containing abundant information about the deep layer D. In the case in which the period Y is equal to or less than 0.1 mm, the proportion of the surface scattered light Ls that spreads into the projection regions of the dark portions from the projection regions of the light portions increases, and the differences between the intensity values Imax and the intensity values Imin consequently decrease, and thus, the information about the surface layer C contained in the surface-layer component image may become insufficient. On the other hand, in the case in which the period Y is equal to or greater than 50 mm, it is not possible for the internal scattered light Ld to reach the centers of the projection regions of the dark portions, the intensity values Imin consequently approach zero, and thus, the information about the deep layer D contained in the deep-layer image may become insufficient.

In this embodiment, although the intensity-distribution changing unit 5 may alternately change, in a non-continuous manner, the intensity distribution of the first illumination light L1 between the two dark/light patterns in which the light portions and the dark portions are inverted relative to each other, as shown in FIGS. 3A to 3F, alternatively, the intensity distribution of the first illumination light L1 may be changed in a continuous manner between the two dark/light patterns.

In the case in which the dark/light patterns are changed in a continuous manner in this way, the imaging unit 6 may execute image-capturing at three or more times at which the positions of the light portions and the dark portions differ from each other, and may image three or more first illumination images, which are treated as one set and in which the positions of the projection regions of the light portions and the projection regions of the dark portions differ from each other. The separating-processing unit 71 may create the surface-layer component image and the deep-layer component image from the three or more first illumination images. In this case, because three or more intensity values are obtained for pixels at the respective positions, the maximum intensity value may be calculated as Imax and the minimum intensity value may be calculated as Imin.

Figure 11:
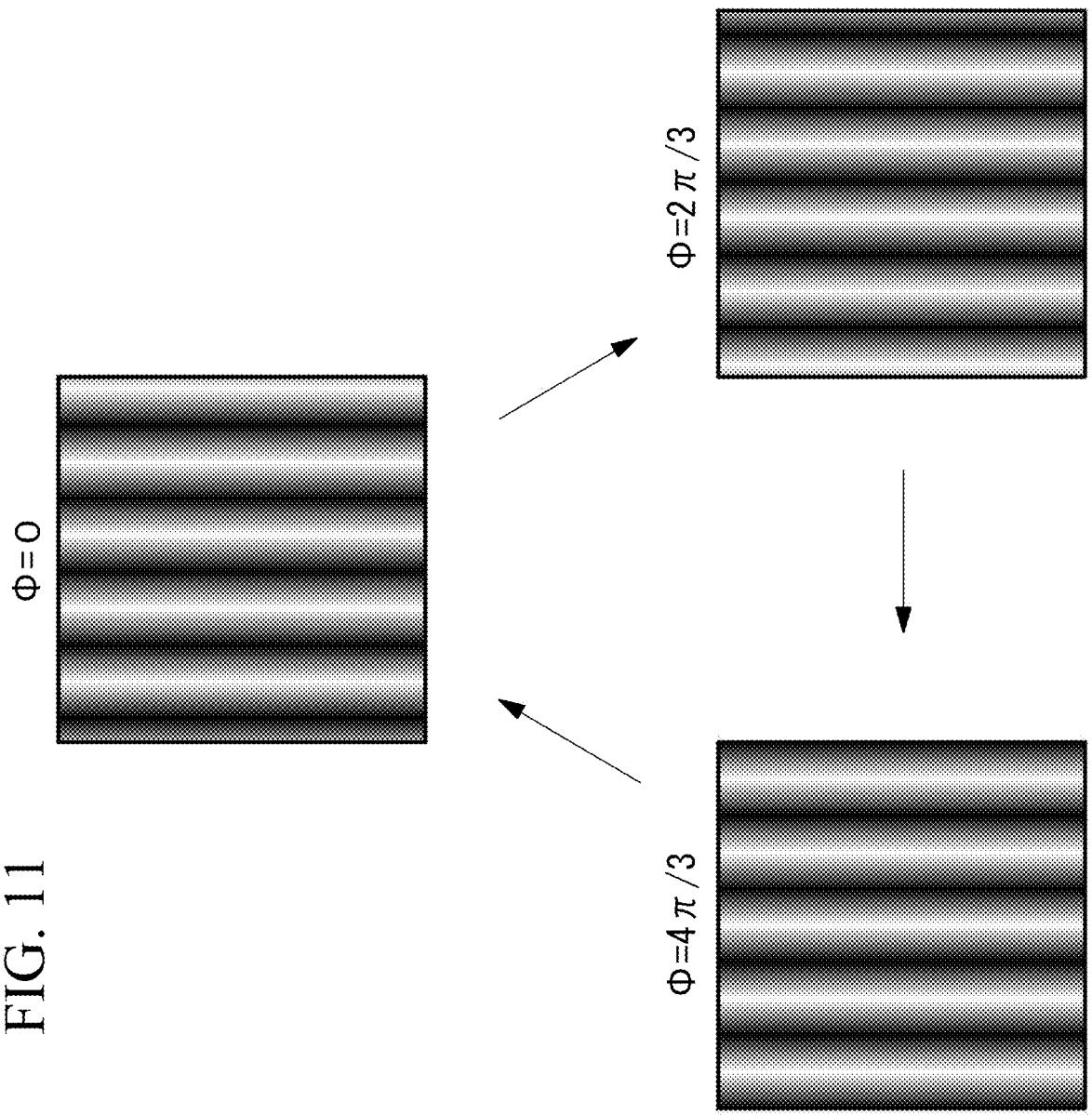
FIG. 11 is a diagram for explaining a method for calculating intensity values Imax and Imin by means of a phase shift method.

In this embodiment, although the intensity values of the two first illumination images, which are treated as one set, are used as the intensity values Imax and Imin, in the case in which the dark/light pattern is a straight-line stripe shape shown in FIGS. 3B and 4B in which the intensity changes in a sinusoidal manner, the intensity values Imax and Imin of the individual pixels may be calculated by means of a phase shift method. With a phase shift method, as shown in FIG. 11, it is possible to determine the maximum intensity values Imax and the minimum intensity values Imin of the individual pixels from three first illumination images, which are treated as one set and in which phases $\Phi$ of the dark/light pattern differ from each other. Therefore, it is possible to create, from a low number of the first illumination images, a surface-layer component image and a deep-layer component image that have the same resolution as the second illumination image.

Figure 12:
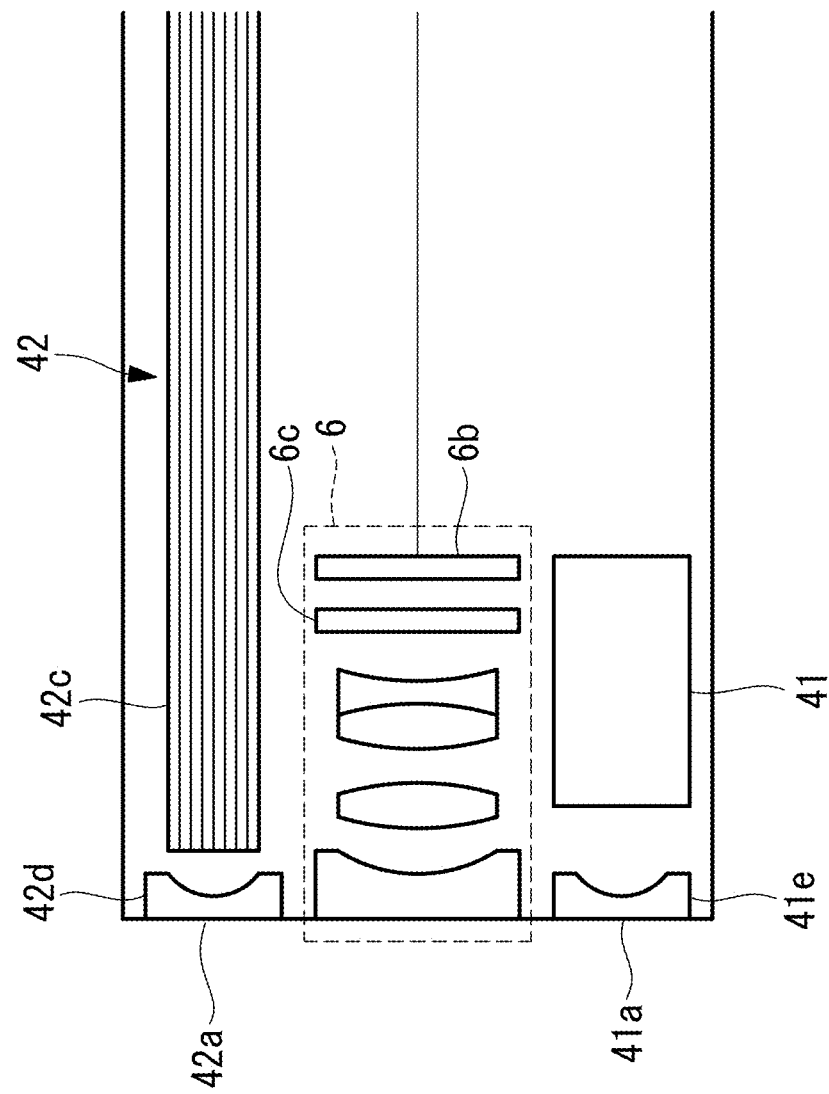
FIG. 12 is a partial configuration diagram of a modification of an endoscope system including a polarizing plate.

In this embodiment, although the high-spatial-frequency first illumination light beam L1 is used in order to remove the specular light beam of the surface B from the surface-layer component image, alternatively, as shown in FIG. 12, a first illumination light beam L1, which is linearly polarized light, may be used.

Specifically, the first illuminating portion 41 emits a first illumination light beam L1, which is linearly polarized light, toward the biological tissue A. Therefore, the first illuminating portion 41 is provided with, as needed, a polarizing plate that converts the first illumination light beam L1 to the linearly polarized light. The first illuminating portion 41 sequentially emits a first illumination light beam having a spatial intensity distribution in which the bright portions and the dark portions are periodically repeated, and a spatially uniform first illumination light beam.

The imaging unit 6 additionally includes a polarizing plate 6c that can be inserted into/retracted from an optical path in the preceding stage of the imaging device 6b, and that has substantially the same polarizing direction as the polarizing direction of the first illumination light L1. The polarizing plate 6c is provided so as to be movable by means of an actuator (not shown) between a position on the optical path and a position away from the optical path. The imaging unit 6 images a total of three first illumination images by executing image capturing when the polarizing plate 6c is disposed on the optical path and when the polarizing plate 6c is retracted from the optical path. Specifically, when the polarizing plate 6c is retracted from the optical path, the imaging unit 6 images two images in which the biological tissue A is irradiated with first illumination lights having intensity distributions in which the positions of the light portions and the dark portions are exchanged with each other by the intensity-distribution changing unit 5. When the polarizing plate 6c is disposed on the optical path, the imaging unit 6 images one image in which the biological tissue A is radiated with a spatially uniform first illumination light.

The specular light Lr is linearly polarized light having substantially the same polarizing direction as that of the first illumination light L1, whereas the scattered lights Ls and Ld do not have a specific polarized state. Therefore, when the polarizing plate 6c is disposed on the optical path of the imaging unit 6, the scattered lights Ls and Ld are removed by the polarizing plate 6c, and the specular light Lr is selectively made incident on the imaging device 6b. By doing so, a first illumination image (surface image information) in which only the specular light Lr is captured is imaged. This first illumination image is equivalent to the surface-layer component image based on the high-spatial-frequency first illumination light L1.

On the other hand, when the polarizing plate 6c is retracted from the optical path of the imaging unit 6, the scattered lights Ls and Ld are also made incident on the imaging device 6b together with the specular light Lr. By doing so, two first illumination images in which the specular light Lr and the scattered lights Ls and Ld are captured are imaged. These two first illumination images are equivalent to the first illumination image based on the low-spatial-frequency first illumination light L1. The image-processing unit 7 generates a surface-layer component image (surface-layer image information) that contains a large amount of the information about the surface layer C on the basis of the light portions of these two first illumination images, and generates a deep-layer component image (deep-layer image information) that contains a large amount of information about the deep layer D on the basis of the dark portions of these two first illumination images.

The separating-processing unit 71 creates a difference image by using the first illumination image imaged when the polarizing plate 6c is retracted from the optical path instead of the surface-layer component image based on the high-spatial-frequency first illumination light. By utilizing, in this way, the first illumination light L1, which is linearly polarized light, instead of the high-spatial-frequency first illumination light L1, it is also possible to obtain a difference image in which the specular light is removed, and thus, it is possible to create a natural synthesized image and a final synthesized image that do not contain noise originating from the specular light.

It is preferable that periods Z of the light portions and the dark portions of the first illumination light L1, which has an intensity distribution, on the surface B satisfy conditional expression (4) below, as with the above-described low-spatial-frequency first illumination light L1:

$$0.1 \text{ mm} < Z < 5 \text{ mm} \tag{4}.$$

As a result, the following aspect is read from the above described embodiment of the present invention.

A first aspect of is an endoscope system including: a first illuminating unit that radiates first illumination lights, which have a spatial intensity distribution in which light portions and dark portions are periodically repeated in a cross-section that is orthogonal to an optical axis, onto a subject from a first emitting surface; a second illuminating unit that radiates a second illumination light onto the subject from a second emitting surface that is different from the first emitting surface; an imaging unit that images first illumination images, which are images of the subject irradiated with the first illumination light, and a second illumination image, which is an image of the subject irradiated with the second illumination light; and an image-processing unit that processes the first illumination images and the second illumination image imaged by the imaging unit, wherein the first illuminating unit has an intensity-distribution changing unit that changes the intensity distribution over time so that positions of the bright portions and the dark portions on a surface of the subject are exchanged with each other, and sequentially radiates a first illumination light having low-spatial-frequency, in which the spatial frequency of the intensity distribution is relatively low, and a first illumination light having high-spatial-frequency, in which the spatial frequency of the intensity distribution is relatively high, wherein the imaging unit images at least four images that serves as the first illumination images, wherein the at least four images include images that correspond to the first illumination light having low-spatial-frequency and the first illumination light having high-spatial-frequency, and two images in which the positions of the light portions and the dark portions are exchanged with each other by the intensity-distribution changing unit, and wherein the image-processing unit has a separating-processing unit that separates three of image information for different depths of the subject from the at least four images, and an image-synthesizing unit that processes the second illumination image by using image information other than the image information about the outermost surface side of the subject among the three of image information separated by the separating-processing unit.

With this aspect, the second illumination image is imaged as a result of the imaging unit capturing an image of the subject that is illuminated with the second illumination light coming from the second emitting surface. On the other hand, the four first illumination images are imaged as a result of the imaging unit capturing, at least four times, images of the subject that is illuminated with the first illumination light coming from the first emitting surface.

In the projection regions of the bright portions on the subject, the specular light generated at a surface of the subject, the surface scattered light scattered in the surface layer of the subject, and the deep-layer scattered light scattered in the deep layer of the subject are generated. On the other hand, in the projection regions of the dark portions on the subject, the deep-layer scattered light, which spreads into the projection regions of the dark portions from the projection regions of the light portions, is generated in a dominant manner. Therefore, image information that contains a large amount of information about the surface and the surface layer is obtained from the bright portions in the respective first illumination images, and image information that contains a large amount of information about the deep layer is obtained from the dark portions in the respective first illumination images. In other words, by exchanging the positions of the light portions and the dark portions projected onto the subject with each other by changing the intensity distributions of the first illumination lights over time, it is possible to image both the information about the surface layer and the information about the deep layer at the individual positions on the subject. In addition, the depths of the image information based on the light portions in the first illumination image depend on the periods of the light portions and the dark portions on the subject, and image information about a shallower position is obtained with an increase in the spatial frequency of the intensity distributions and a decrease in the periods of the light portions and the dark portions. In other words, the light portions of the first illumination images obtained by using the first illumination light having high-spatial-frequency contain a large amount of information about the surface. Therefore, it is possible to separate, from the four first illumination images, three of image information that contain large amounts of information about the surface, the surface layer, and the deep layer of the subject, respectively.

In this case, because the positions of the first emitting surface from which the first illumination light is emitted and the second emitting surface from which the second illumination light is emitted are different from each other, the position of the specular light in the first illumination image and the position of the specular light in the second illumination image are displaced from each other. Information about the specular light generated at the surface of the subject is contained in the image information about the outermost surface side. Therefore, as a result of using two of image information other than the image information about the outermost surface side among the three of image information to process the second illumination image, it is possible to suppress, in the synthesized image, the generation of noise originating from the specular light contained in the first illumination image.

In the above-described first aspect, the separating-processing unit may separate, from the at least four images, three of image information, namely, first surface-layer image information, second surface-layer image information, and deep-layer image information, and may image difference image information by subtracting the first surface-layer image information from the second surface-layer image information, wherein the image-synthesizing unit may process the second illumination image by using the difference image information and the deep-layer image information, and wherein the first surface-layer image information may be image information based on the light portions on the surface of the subject irradiated with the first illumination light having high-spatial-frequency, the second surface-layer image information may be image information based on the light portions on the surface of the subject irradiated with the first illumination light having low-spatial-frequency, the deep-layer image information may be image information based on the dark portions on the surface of the subject irradiated with the first illumination light having low-spatial-frequency, and the difference image information may be image information other than the image information about the outermost surface side of the subject.

In this way, as a result of subtracting the first surface-layer image information obtained by using the first illumination light having high-spatial-frequency from the second surface-layer image information, the information about the specular light at the surface is removed, difference information containing a large amount of information about the surface layer is obtained, and thus, it is possible to create a synthesized image in which the visibility of structures in the surface is enhanced by using the difference image information.

In the above-described first aspect, it is preferable that periods X of the light portions and the dark portions of the first illumination light having high-spatial-frequency on the subject and periods Y of the light portions and the dark portions of the first illumination light having low-spatial-frequency on the subject satisfy conditional expressions (1) to (3) below:

$$0.005 \text{ mm} < X < 2.0 \text{ mm} \tag{1};$$

$$0.1 \text{ mm} < Y < 50 \text{ mm} \tag{2}; \text{ and}$$

$$X < Y \tag{3}.$$

As a result of satisfying conditional expression (1), first surface-layer image information in which the information about the specular light at the surface is dominant is obtained. By using such first surface-layer image information, it is possible to obtain difference image information in which the specular light is removed in a highly precise manner.

As a result of satisfying conditional expression (2), it is possible to separate, in a spatially highly precise manner, the internal scattered light from the specular light and the surface scattered light, and it is possible to obtain a good second surface-layer component image and deep-layer component image.

A second aspect of the present invention is an endoscope system including: a first illuminating unit that sequentially radiates an illumination light, which includes linearly polarized light and has a spatial intensity distribution in which light portions and dark portions are periodically repeated in a beam cross-section that is orthogonal to an optical axis, and a spatially uniform illumination light onto an subject from a first emitting surface as a first illumination light; a second illuminating unit that radiates a second illumination light onto the subject from a second emitting surface that is different from the first emitting surface; an imaging unit that images first illumination images, which are images of the subject irradiated with the first illumination light, and a second illumination image, which is an image of the subject irradiated with the second illumination light; and an image-processing unit that processes the first illumination images and the second illumination image imaged by the imaging unit, wherein the first illuminating unit has an intensity-distribution changing unit that changes the intensity distribution over time so that positions of the light portions and the dark portions on a surface of the subject are exchanged with each other, wherein the imaging unit has a polarizing plate that has substantially the same polarizing direction as the polarizing direction of the first illumination light and that can be inserted into/retracted from an optical path, wherein the first illumination images include at least two images that are imaged when the polarizing plate is retracted from the optical path and in which the first illumination light that has the intensity distribution and in which the positions of the light portions and the dark portions are exchanged with each other by the intensity-distribution changing unit is radiated, and an image that is imaged when the polarizing plate is disposed on the optical path and in which the spatially uniform first illumination light is radiated, and wherein the image-processing unit has a separating-processing unit that separates three of image information for different depths of the subject from the at least four images, and an image-synthesizing unit that processes the second illumination image by using image information other than the image information about the outermost surface side of the subject among the three of image information separated by the separating-processing unit.

The specular light has substantially the same polarizing direction as the polarizing direction of the first illumination light, whereas the surface scattered light and the internal scattered light do not have a specific polarized state. Because of this, the information about the surface becomes dominant in the first illumination image obtained when the polarizing plate is disposed on the optical path. Therefore, it is possible to separate the three of image information that contain large amounts of information about the surface, the surface layer, and the deep layer, respectively, from the first illumination image obtained when the polarizing plate is retracted from the optical path and the light portions and the dark portions of two first illumination images obtained when the polarizing plate is disposed on the optical path.

In the above-described second aspect, the separating-processing unit may separate three of image information, namely, surface-layer image information, deep-layer image information, and surface image information, and may image difference image information by subtracting the surface image information from the surface-layer image information, wherein the image-synthesizing unit may process the second illumination image by using the difference image information and the deep-layer image information, and wherein the surface-layer image information may be image information based on the light portions in the first illumination image of the subject irradiated with the first illumination light having the spatial intensity distribution, the deep-layer image information may be image information based on the dark portions in the first illumination image of the subject irradiated with the first illumination light having the spatial intensity distribution, and the surface image information may be image information based on the first illumination image of the subject irradiated with the spatially uniform first illumination light.

In this way, by subtracting the first illumination image obtained when the polarizing plate is disposed on the optical path from the surface-layer image information separated from the first illumination image obtained when the polarizing plate is retracted from the optical path, the difference image information that contains a large amount of information about the surface layer in which the information about the specular light at the surface is removed, and thus, it is possible to create a synthesized image in which the visibility of the structures in the surface layer is enhanced by using the difference image information.

In the above-described second aspect, periods Z of the light portions and the dark portions of the first illumination light, which has the spatial intensity distribution, on the surface of the subject may satisfy conditional expression (4) below:

$$0.1 \text{ mm} < Z < 50 \text{ mm} \tag{4}$$

In the above-described first and second aspects, the intensity distribution of the first illumination light may have a striped shape in which the light portions and the dark portions that are band-like are alternately repeated in a width direction.

By doing so, it is possible to effectively separate the internal scattered light by means of a simple dark/light pattern. In addition, in order to exchange the positions of the light portions and the dark portions of the striped intensity distribution with each other, the light portions and the dark portions of the intensity distribution may be moved only in the width direction of the stripes; therefore, it is possible to easily change the intensity distribution of the first illumination light over time.

In the above-described first and second aspects, the first illumination light may be a single wavelength light.

By doing so, it is possible to use a small light source, such as a laser light source or an LED, to generate the first illumination light. In addition, it is possible to easily generate the first illumination light that has light portions and dark portions with high contrast and that has high luminance.

REFERENCE SIGNS LIST 1 endoscope system
2 endoscope
3 main body
41 first illuminating unit
42 second illuminating unit
5 intensity-distribution changing unit
6 imaging unit
6c polarizing plate
7 image-processing unit
8 display apparatus
A biological tissue (subject)
B surface C surface layer
D deep layer
L1 first illumination light
L2 second illumination light
Lr specular light beam
Ls surface scattered light
Ld internal scattered light

The invention claimed is:

1. An endoscope system comprising:
a first illuminating unit that is configured to radiate first illumination lights, which have a spatial intensity distribution in which light portions and dark portions are periodically repeated in a beam cross-section that is orthogonal to an optical axis, onto a subject from a first emitting surface;
a second illuminating unit that is configured to radiate a second illumination light onto the subject from a second emitting surface that is different from the first emitting surface;
an imaging unit that is configured to image first illumination images, which are images of the subject irradiated with the first illumination light, and a second illumination image, which is an image of the subject irradiated with the second illumination light; and
an image-processing unit that is configured to process the first illumination images and the second illumination image imaged by the imaging unit,
wherein the first illuminating unit has an intensity-distribution changing unit that
changes the intensity distribution over time so that positions of the light portions and the dark portions on a surface of the subject are exchanged with each other, and
sequentially radiates a first illumination light having low-spatial-frequency, in which the spatial frequency of the intensity distribution is relatively low, and a first illumination light having high-spatial-frequency, in which the spatial frequency of the intensity distribution is relatively high,
wherein the imaging unit images at least four images that serve as the first illumination images,
wherein the at least four images include images that correspond to the first illumination light having low-spatial-frequency and the first illumination light having high-spatial-frequency, and two images in which the positions of the light portions and the dark portions are exchanged with each other by the intensity-distribution changing unit, and
wherein the image-processing unit has
a separating-processing unit that is configured to separate three image information for different depths of the subject from the at least four images, and
an image-synthesizing unit that is configured to process the second illumination image by using an image information other than an image information about the outermost surface side of the subject among the three image information separated by the separating-processing unit.

2. The endoscope system according to claim 1,
wherein the separating-processing unit
separates, from the at least four images, three of image information, namely, first surface-layer image information, second surface-layer image information, and deep-layer image information, and
obtains difference image information by subtracting the first surface-layer image information from the second surface-layer image information,
wherein the image-synthesizing unit processes the second illumination image by using the difference image information and the deep-layer image information, and
wherein the first surface-layer image information is image information based on the light portions on the surface of the subject irradiated with the first illumination light having high-spatial-frequency,
the second surface-layer image information is image information based on the light portions on the surface of the subject irradiated with the first illumination light having low-spatial-frequency,
the deep-layer image information is image information based on the dark portions on the surface of the subject irradiated with the first illumination light having low-spatial-frequency, and
the difference image information is image information other than the image information about the outermost surface side of the subject.

3. The endoscope system according to claim 2,
wherein periods X of the light portions and the dark portions of the first illumination light having low-spatial-frequency on the subject and periods Y of the light portions and the dark portions of the first illumination light having low-spatial-frequency on the subject satisfy conditional expressions (1) to (3) below:

$$0.005 \text{ mm} < X < 2.0 \text{ mm} \quad (1);$$

$$0.1 \text{ mm} < Y < 50 \text{ mm} \quad (2); \text{ and}$$

$$X < Y \quad (3).$$

4. The endoscope system according to claim 3,
wherein the separating-processing unit
separates three of image information, namely, surface-layer image information, deep-layer image information, and surface image information, and
images difference image information by subtracting the surface image information from the surface-layer image information,
wherein the image-synthesizing unit processes the second illumination image by using the difference image information and the deep-layer image information, and
wherein the surface-layer image information is image information based on the light portions in the first illumination image of the subject irradiated with the first illumination light having the spatial intensity distribution,
the deep-layer image information is image information based on the dark portions in the first illumination image of the subject irradiated with the first illumination light having the spatial intensity distribution, and
the surface image information is image information based on the first illumination image of the subject irradiated with the spatially uniform first illumination light.

5. The endoscope system according to claim 4,
wherein periods Z of the light portions and the dark portions of the first illumination light, which has the spatial intensity distribution, on the surface of the subject satisfy conditional expression (4) below:

$$0.1 \text{ mm} < Z < 50 \text{ mm} \quad (4).$$

6. The endoscope system according to claim 1,
wherein the intensity distribution of the first illumination light has a striped shape in which the light portions and the dark portions that are band-like are alternately repeated in a width direction.

7. The endoscope system according to claim 1,
wherein the first illumination light is a single wavelength light.

8. An endoscope system comprising:
a first illuminating unit that is configured to sequentially radiate an illumination light, which includes linearly polarized light and has a spatial intensity distribution in which light portions and dark portions are periodically repeated in a beam cross-section that is orthogonal to an optical axis, and a spatially uniform illumination light onto a subject from a first emitting surface as a first illumination light;
a second illuminating unit that is configured to radiate a second illumination light onto the subject from a second emitting surface that is different from the first emitting surface;
an imaging unit that is configured to image first illumination images, which are images of the subject irradiated with the first illumination light, and a second illumination image, which is an image of the subject irradiated with the second illumination light; and
an image-processing unit that is configured to process the first illumination images and the second illumination image imaged by the imaging unit,
wherein the first illuminating unit has an intensity-distribution changing unit that is configured to change the intensity distribution over time so that positions of the light portions and the dark portions on a surface of the subject are exchanged with each other,
wherein the imaging unit has a polarizing plate that has substantially the same polarizing direction as the polarizing direction of the first illumination light and that is inserted into/retracted from an optical path,
wherein the first illumination images include at least two images that are imaged when the polarizing plate is retracted from the optical path and in which the first illumination light that has the intensity distribution and in which the positions of the light portions and the dark portions are exchanged with each other by the intensity-distribution changing unit is radiated, and
an image that is imaged when the polarizing plate is disposed on the optical path and in which the spatially uniform first illumination light is radiated, and
wherein the image-processing unit has
a separating-processing unit that is configured to separate three image information having different depths of the subject, and
an image-synthesizing unit that is configured to process the second illumination image by using an image information other than an image information about the outermost surface side of the subject among the three image information separated by the separating-processing unit.

9. The endoscope system according to claim 8,
wherein the intensity distribution of the first illumination light has a striped shape in which the light portions and the dark portions that are band-like are alternately repeated in a width direction.

10. The endoscope system according to claim 8,
wherein the first illumination light is a single wavelength light.

* * * * *